(12) United States Patent
Volpert et al.

(10) Patent No.: US 8,198,406 B2
(45) Date of Patent: Jun. 12, 2012

(54) METHODS AND COMPOSITIONS FOR INHIBITING ANGIOGENESIS

(75) Inventors: Olga Volpert, Wilmette, IL (US); Yelena Mirochnik, Chicago, IL (US)

(73) Assignee: Northwestern University, Evanston, IL (US)

( * ) Notice: Subject to any disclaimer, the term of this patent is extended or adjusted under 35 U.S.C. 154(b) by 489 days.

(21) Appl. No.: 12/267,031

(22) Filed: Nov. 7, 2008

(65) Prior Publication Data

US 2010/0331263 A1    Dec. 30, 2010

Related U.S. Application Data

(60) Provisional application No. 60/986,124, filed on Nov. 7, 2007.

(51) Int. Cl.
*A61K 38/00* (2006.01)
*A61K 35/00* (2006.01)

(52) U.S. Cl. ................................ 530/326; 514/13.3

(58) Field of Classification Search .......................... None
See application file for complete search history.

(56) References Cited

U.S. PATENT DOCUMENTS

| | | | |
|---|---|---|---|
| 4,885,171 A * | 12/1989 | Surendra et al. ............... | 424/122 |
| 5,051,448 A | 9/1991 | Shashoua | |
| 5,169,862 A | 12/1992 | Burke, Jr. et al. | |
| 5,192,746 A | 3/1993 | Lobl et al. | |
| 5,539,085 A | 7/1996 | Bischoff et al. | |
| 5,559,103 A | 9/1996 | Gaeta et al. | |
| 5,576,423 A | 11/1996 | Aversa et al. | |
| 6,797,691 B1 * | 9/2004 | Bouck et al. ................... | 514/13.3 |

FOREIGN PATENT DOCUMENTS

WO    WO 2004080148 A2 *   9/2004

OTHER PUBLICATIONS

Soluble Flt-1 (Soluble VEGFR-1), a Potent Natural Antiangiogenic Molecule in Mammals, is Phylogenetically Conserved in Avians Biochemical and Biophysical Research Communications vol. 291, Issue 3, Mar. 1, 2002, pp. 554-559.*
Eldred et al., "Orally active non-peptide fibrinogen receptor (GpIIb/IIIa) antagonists: identification of 4-[4-[4-(aminoiminomethyl)phenyl]-1-piperazinyl]-1-piperidineacetic acid as a long-acting, broad-spectrum antithrombotic agent" 1994 J. Med. Chem. 37:3882.
Fernandez-Garcia et al., "Pigment Epithelium-derived Factor as a Multifunctional Antitumor Factor" 2007 J Mol Med 85:15-22.
Ferrara et al., "Vascular endothelial growth factor: basic science and clinical progress." 2004 Endocr Rev. 25 (4):581-611.
Filleur et al., "Two functional epitopes of pigment epithelial-derived factor block angiogenesis and induce differentiation in prostate cancer" 2005 Cancer Res 65 5144.
Gasparini "Angiogenesis research up to 1996. A commentary on the state of art and suggestions for future studies" 1996 Eur. J. Cancer 32A(14):2379-2385.
Guedez et al., "Quantitative assessment of angiogenic responses by the directed in vivo angiogenesis assay" 2003 Am J Pathol 162 1431.
Jung et al., "Expression of vascular endothelial growth factor in invasive ductal carcinoma of the breast and the relation to angiogenesis and p53 and HER-2/neu protein expression" 2002 Appl Immunohistochem Mol Morphol. Dec. 2002;10(4):289-95.
Kerbel and Kamen, "The Anti-Angiogenic Basis of Metronomic Chemotherapy" 2004 Nat Rev Cancer. Jun. 2004;4(6):423-36.
Ku et al., "Potent non-peptide fibrinogen receptor antagonists which present an alternative pharmacophore" 1995 J. Med. Chem. 38:9-12.
Mirochnik et al., "Pigment Epithelial Derived Factor: Development of Angiogenic Peptides" 2006 European J Cancer 4S (12): 37.
Notari et al., "Identification of a lipase-linked cell membrane receptor for pigment epithelium-derived factor" 2006 J Biol Chem 281 38022.
Presentation: Symposium on "Molecular Targets and Cancer Therapeutics" Prague, Czech Republic Nov. 7-10, 2006.
Seo et al., "TIMP-2 mediated inhibition of angiogenesis: an MMP-independent mechanism" 2003 Cell 114-171.
Wang et al., "CD97, an adhesion receptor on inflammatory cells, stimulates angiogenesis through binding integrin counterreceptors on endothelial cells" 2005 Blood 105 2836-44.

* cited by examiner

*Primary Examiner* — Anish Gupta
*Assistant Examiner* — Jeanette Lieb
(74) *Attorney, Agent, or Firm* — Casimir Jones, S.C.

(57) ABSTRACT

The present invention relates to methods and compositions for modulating angiogenesis. In particular, the present invention relates to Pigment Epithelial-derived Factor (PEDF) fragments for use in modulating angiogenesis and treating angiogenesis mediated disease.

10 Claims, 10 Drawing Sheets

FIGURE 7

SEQ ID NO:50   (accession no. AAP36928)

MQAIVLLLCIGALLGHSSCQNPASPPEEGSPDPDSTGALVEEEDPFFKVPVNRLAAAVSNFGYDLYRVRSSTSPTTN
VLLSPLSVATALSALSLGAEQRTESIIRALYYDLISSPDIHGTYKELLDTVTAPQKNLKSASRIVFEKKLRIKSSF
VAPLEKSYGTRPRVLTGNPRLDLQEINNWVQAQMKGKLARSTKEIPDEIGILLLGVAHFKGQWVTKFDSRKTSLED F
YLEEERTVRVPMMSDPKAVLRYGLDSDLSCKIAQLPLTGSMSLLFFLPLKVTQNLTLIEESLTSEFIHDIDRELKTV
QAVLTVPKLKLSYEGEVTKSLQEMKLQSLFDSPDFSKITGKPIKLTQVEHRAGFEWNEDGAGTTPSPGLQPAHLTF P
LDYHLNQPFIFVLRDTDTGALLFIGKILDPRGPL

FIGURE 10

SEQ ID NO:101 (accession no. AAH13984)

```
  1 mqalvlllci gallqbsscq npasppeeqs pdpdstgalv esedpffkvp vsklsaavsn
 61 fgydlyrvrs smspttavll splsvatals alslgaeqrt esiihralyy ditsspdihq
121 tykellstvt arqknlkaas rivfekklrl kssfvaplek sygtrprvlt gnprldlqei
181 snwvqaqekg klarstkslp delslllgv ahfkgqwvtk fdsrktsled fyldeertvr
241 vpmmsdpkav lrygldsdls cklaqlpltg smsiifflpl kvtqnlrlie esltsefihd
301 idrelktvqa vltvpklkls yegevtkslq emklqalfds pdfskitqkp ikltqvehra
361 gfewnedgag ttpspglqps hltfpldyhl nqpfifvird tdtgallfig kildprgp
```

METHODS AND COMPOSITIONS FOR INHIBITING ANGIOGENESIS

The present application claims priority to U.S. Provisional Application Ser. No. 60/986,124, filed Nov. 7, 2007, which is herein incorporated by reference in its entirety.

This invention was made with government support under grant number W81XWH-0-6-1-0103 awarded by the Army/MRMC and grant number R01HL068033 awarded by the National Institutes of Health. The government has certain rights in the invention.

FIELD OF THE INVENTION

The present invention relates to methods and compositions for modulating angiogenesis. In particular, the present invention relates to Pigment Epithelial-derived Factor (PEDF) fragments for use in modulating angiogenesis and treating angiogenesis mediated disease.

BACKGROUND OF THE INVENTION

Tumor angiogenesis is a complex process in which new blood vessels are formed in response to interactions between tumor cells and endothelial cells (ECs), growth factors, and extracellular matrix components. Tumor vessels promote growth and progression of human solid tumors (e.g., cancer of the liver, bladder, and prostate). New tumor blood vessels penetrate into cancerous growths, supplying nutrients and oxygen and removing waste products (Jung et al., 2002; Folkman, 2002; Kerbel and Kamen, 2004; Stupack and Cheresh, 2004). A large number of studies have demonstrated that tumor cells secrete angiogenic growth factors to stimulate EC proliferation and to induce angiogenesis. Among them, vascular endothelial growth factor (VEGF) is one of the most potent angiogenic factors, and it is overexpressed in many human cancers (Jung et al., 2002).

Targeting VEGF for human cancer therapy has shown some promise in the treatment of colorectal cancer, demonstrating the potential for cancer therapy based upon blocking angiogenesis (Ferrara et al., 2004). However, targeting VEGF for human cancer therapy has not been successful in a multiplicity of other tumor types, suggesting that other factors or components also play a critical role in tumor angiogenesis (Jung et al., 2002; Kerbel and Kamen, 2004). The identification of these factors and components have important implications in human cancer therapy.

Thus, there is need for the identification of other factors or components that are involved in tumor angiogenesis. Furthermore, new compositions and methods are required to target these factors that can be used to treat cancer (e.g., to inhibit angiogenesis, whose loss is associated with cancer).

SUMMARY OF THE INVENTION

The present invention relates to methods and compositions for modulating angiogenesis. In particular, the present invention relates to Pigment Epithelial-derived Factor (PEDF) fragments for use in modulating angiogenesis and treating angiogenesis mediated disease.

In some embodiments, the present invention provides compositions comprising an isolated peptide, wherein the peptide consists of an amino acid sequence selected from: SEQ ID NOs:2, 12, 13, 22, 23, 33, 34, 41, 42, 43-49, 52, 53, 62, 63, 73, 74, 84, 85, and 92-100. In other embodiments, the peptide comprises, or consists of, SEQ ID NOs: 1-49 and 52-100. In certain embodiments, one or more of the amino acid in any of these sequences are substituted with modified versions of the appropriate amino acid or amino acids that do not detrimentally affect the anti-angiogenic activity of the peptide.

In some embodiments, the present invention provides methods of inhibiting angiogenesis, comprising: contacting a tissue (e.g., exhibiting angiogenesis) with a composition comprising an isolated peptide (e.g., under conditions such that angiogenesis is decreased in the tissue), wherein the peptide comprises, or consists of, an amino acid sequence selected from: SEQ ID NOs:2, 12, 13, 22, 23, 33, 34, 41, 42, 43-49, 52, 53, 62, 63, 73, 74, 84, 85, and 92-100. In certain embodiments, the peptide comprises, or consists of, SEQ ID NOs: 1-49 and 52-100. In particular embodiments, the methods further comprise the step of administering a second agent to the tissue (e.g., anti-cancer agent or anti-angiogenic agent). In particular embodiments, the tissue is cancerous tissue. In further embodiments, the tissue is in a subject. In particular embodiments, the composition is administered to the subject at a dosage of between 5-150 mg/kg or between 10-75 mg/kg (e.g., 10 mg/kg ... 25 mg/kg ... 50 mg/kg ... 60 mg/kg ... 75 mg/kg ... 100 mg/kg ... 125 mg/kg ... or 150 mg/kg). In certain embodiments, the subject has ocular neovascularization or cancer.

In certain embodiments, the peptide exhibits anti-angiogenic or anti-cancer activity. In particular embodiments, the peptide consists of (or consists essentially of) the amino acid sequence shown in SEQ ID NO:2 or SEQ ID NO:52.

In further embodiments, the compositions further comprise a non-amino acid chemical moiety, wherein the non-amino acid chemical moiety is attached to, or associated with, the peptide. In certain embodiments, the chemical moiety is a fluorescent compound or a compound intended to aid in the in vivo delivery of the peptide.

In some embodiments, the compositions further comprise an anti-cancer agent different from the peptide. In certain embodiments, the anti-cancer agent is selected from the group consisting of: rapamycin, Alkylating agents (e.g., Cisplatin and carboplatin, oxaliplatin, mechlorethamine, cyclophosphamide, chlorambucil), Anti-metabolites (e.g., azathioprine, or mercaptopurine), Plant alkaloids and terpenoids (e.g., vinca alkaloids and taxanes), Vinca alkaloids (e.g, Vincristine, Vinblastine, Vinorelbine, and Vindesine), Podophyllotoxin, Taxanes (e.g., paclitaxel), Topoisomerase inhibitors (e.g., camptothecins: irinotecan and topotecan, amsacrine, etoposide, etoposide phosphate, and teniposide), Antitumour antibiotics (e.g., dactinomycin), and Monoclonal antibodies (e.g., trastuzumab, cetuximab, rituximab, and Bevacizumab).

In particular embodiments, the compositions further comprise a physiological tolerable buffer. In other embodiments, the compositions further comprise an anti-angiogenic agent different from the peptide. In certain embodiments, the anti-angiogenic agent is selected from the group consisting of: soluble VEGFR-1, NRP-1, Angiopoietin 2, TSP-1, TSP-2, angiostatin and related molecules, endostatin, vasostatin, calreticulin, platelet factor-4, TIMP, CDAI, Meth-1, Meth-2, IFN-α, -β and -γ, CXCL10, IL-4, IL-12 IL-18, prothrombin (kringle domain-2), antithrombin III fragment, prolactin, VEGI, SPARC, osteopontin, maspin, canstatin, proliferin-related protein, and restin. In particular embodiments, the compositions are pharmaceutical compositions (e.g., suitable for injection into an animal or a human).

In some embodiments, the present invention provides a composition comprising an isolated fragment of pigment epithelial-derived factor (PEDF) (e.g., a fragment comprising or consisting of: SEQ ID NO:2, SEQ ID NO:1, SEQ ID NOs:3-49, SEQ ID NOs:52-100, or mimetics, variants, or derivatives thereof), wherein the fragment of PEDF exhibits anti-angiogenic activity. In other embodiments, the present invention provides a composition comprising an isolated peptide comprising, or consisting of, or consisting essentially of: SEQ ID NOs:2, 12, 13, 22, 23, 33, 34, 41-49, 52, 53, 62, 63, 73, 74, 84, 85, and 92-100, or combinations thereof (e.g., wherein the peptide has anti-angiogenic activity). In some embodiments, the composition further comprises a second fragment of PEDF (e.g., a fragment comprising or consisting of amino acids 78-121 of PEDF). In some embodiments, the composition further comprises additional agents with anti-angiogenesis or anti-cancer activity. In some embodiments, the composition is a pharmaceutical composition.

The present invention further provides a method of inhibiting angiogenesis, comprising: contacting a tissue exhibiting angiogenesis with a fragment of PEDF under conditions such that angiogenesis is decreased in the tissue. In some embodiments, the fragment comprises or consists of: SEQ ID NO:2, SEQ ID NO:1, SEQ ID NOs:3-49, SEQ ID NOs:52-100, or mimetics, variants, or derivatives thereof. In further embodiments, the peptide comprises, or consists of, or consists essentially of: SEQ ID NOs:2, 12, 13, 22, 23, 33, 34, 41-49, 52, 53, 62, 63, 73, 74, 84, 85, and 92-100 or combinations thereof (e.g., wherein the peptide has anti-angiogenic activity). In some embodiments, the method further comprises the step of administering a second agent to the tissue. In some embodiments, the second agent is a second fragment of PEDF (e.g., comprising or consisting of amino acids 78-121 of PEDF) or a known anti-angiogenic or anti-cancer agent. In some embodiments, the tissue is cancerous tissue. In some embodiments, the tissue is in a subject.

BRIEF DESCRIPTION OF THE FIGURES

FIG. 3A), 18-mer (SEQ ID NO:2; FIG. 3B), and 23-mer (SEQ ID NO:3; FIG. 3C).

FIG. 4A shows immunofluorescent staining of human endothelial cells. Confluent HMVEC cells growing on coverslips were incubated overnight in low serum media (0.2% FBS in MCDB)±PEDF peptides in the presence or absence of bFGF. ApopTag Fluorescein kit (Chemicon) was used to determine apoptotic cells. FIG. 4B shows quantitative analysis of apoptosis. 3-5 fields (10×) were analyzed with epi-fluorescent microscope, and cells were counted using MetaMorph software. Apoptotic (FITC positive) cells were calculated as a % of total cells stained with PI per field.

FIGS. 5A and 5B show the results of a corneal angiogenesis assay. The 34 mer and 18-mer peptides were incorporated with bFGF (50 ng/pellet) into slow-release sucralfate pellets, which were surgically mplanted into the cornea of anesthetized mice, 0.5-1 mm from the vascular limbus. The responses were scored on day 5 post implantation and the ingrowth of blood vessels from the cornea to the pellet was considered a positive response. The responses were scored as positive corneas of total implanted: statistical significance was evaluated with Fisher's Exact test. P<0.05 was considered significant. FIG. 5A shows photographs of representative corneas. FIG. 5B shows tabulated results of the cornea assay. FIGS. 5C and 5D shows the directed in vivo angiogenesis assay (DIVAA) for the 34-mer, 23-mer, and 18-mer peptides. The peptides were incorporated with a mix of bFGF and VEGF (37.5 and 12.5 ng/ml, respectively) into angioreactors filled with matrigel. The reactors were implanted s.c onto the flanks of the nude mice. On day 7, The reactors were harvested and photographed (5C). Endothelial cells collected from implants by dilution/centrifugation, stained with FITC-lectin and quantified by flow cytometry (5D). In both assays the 18-mer showed the best anti-angiogenic characteristics. The 23-mer failed to inhibit angiogenesis in the DIVAA assay.

FIG. 7 shows the amino acid sequence of a full-length PEDF peptide (SEQ ID NO:50), which is accession number AAP36928.

FIG. 10 shows the amino acid sequence of a full-length PEDF peptide (SEQ ID NO:101), which is accession number AAH13984.

DEFINITIONS

Figure 1:
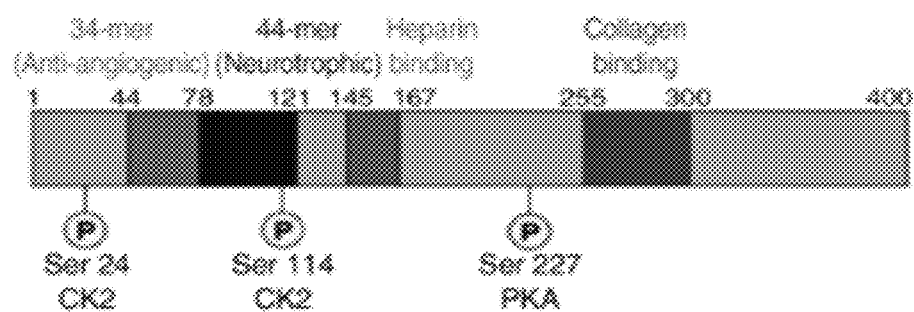
FIG. 1 shows a schematic representation of identified functional domains of PEDF, including major phosphorylation sites and domains known to be critical for interactions with extracellular matrix.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "effective amount" refers to the amount of a composition (e.g., a PEDF peptide) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) (e.g., a PEDF peptide and one or more other agents such as an anti-cancer agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a PEDF peptide) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DESCRIPTION OF THE INVENTION

Angiogenesis is the fundamental process by which new blood vessels are formed. The process involves the migration of vascular endothelial cells into tissue followed by the condensation of such endothelial cells into vess. Angiogenesis may be induced by an exogenous angiogenic agent or may be the result of a natural condition. The process is essential to a variety of normal body activities such as reproduction, development and wound repair. Although the process is not completely understood, it involves a complex interplay of molecules that stimulate and molecules that inhibit the growth and migration of endothelial cells, the primary cells of the capillary blood vessels. Under normal conditions, these molecules appear to maintain the microvasculature in a quiescent state (i.e., without capillary growth) for prolonged periods which can last for several years or even decades. The turnover time for an endothelial cell is about one thousand days. However, under appropriate conditions (e.g., during wound repair), these same cells can undergo rapid proliferation and turnover within a much shorter period, and a turnover rate of five days is typical under these circumstances. (See, e.g., Folkman and Shing, 1989, J. Biol. Chem. 267(16):10931-10934; Folkman and Klagsbrun, 1987, Science 235:442-447).

Although angiogenesis is a highly regulated process under normal conditions, many diseases (characterized as "angiogenic diseases") are driven by persistent unregulated angiogenesis. In such disease states, unregulated angiogenesis can either cause a particular disease directly or exacerbate an existing pathological condition. For example, ocular neovascularization has been implicated as the most common cause of blindness and underlies the pathology of approximately twenty diseases of the eye. In certain previously existing conditions such as arthritis, newly formed capillary blood vessels invade the joints and destroy cartilage. In diabetes, new capillaries formed in the retina invade the vitreous humor and bleed, causing blindness. The compositions and methods of the present invention may employed to treat such angiogenic diseases.

Both the growth and metastasis of solid tumors are also angiogenesis-dependent (See, e.g., Folkman, 1986, J. Cancer Res. 46:467-473; Folkman, 1989, J. Nat. Cancer Inst. 82:4-6; Folkman et al. 1995, "Tumor Angiogenesis," Chapter 10, pp. 206-32, in The Molecular Basis of Cancer, Mendelsohn et al., eds. (W. B. Saunders)). It has been shown, for example, that tumors which enlarge to greater than about 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (See, e.g., Weidner 1991, New Eng. J. Med. 324(1):1-8). When used as drugs in tumor-bearing animals, natural inhibitors of angiogenesis can prevent the growth of small tumors (See, e.g., O'Reilly et al., 1994, Cell 79:315-328). Indeed, in some protocols, the application of such inhibitors leads to tumor regression and dormancy even after cessation of treatment (See, e.g., O'Reilly et al., 1997, Cell 88:277-285). Moreover, supplying inhibitors of angiogenesis to certain tumors can potentiate their response to other therapeutic regimens (e.g., chemotherapy) (See, e.g., Teischer et al., 1994, Int. J. Cancer 57:920-925). The compositions and methods of the present invention may be used to treat cancer (e.g., by inhibiting tumorigenesis).

Although several angiogenesis inhibitors are currently under development for use in treating angiogenic diseases (See, e.g., Gasparini, 1996, Eur. J. Cancer 32A(14):2379-2385), there are disadvantages associated with these proposed inhibitory compounds. For example, suramin is a potent angiogenesis inhibitor, but, at doses required to reach antitumor activity, causes severe systemic toxicity in humans. Other compounds, such as retinoids, interferons and antiestrogens appear safe for human use but have only a weak anti-angiogenic effect. Still other compounds may be difficult or costly to make. In addition, the simultaneous administration of several different inhibitors of angiogenesis may be needed for truly effective treatment.

I. PEDF Mapping

PEDF is a major angiogenesis inhibitor in the eye. It is secreted at by the retinal pigment epithelium (RPE) and regulated by oxygen levels. PEDF is responsible for the neurotrophic activity secreted by RPE cells. It differentiates retinoblastoma tumor cells and promotes survival of the more differentiated neuronal cells such as cerebellar granule neurons, hippocampal neurons, photoreceptors, and cultured retinal neurons.

The complications of diabetes mellitus, kidney failure and loss of vision involve major vascular abnormalities. Vascular beds in the posterior eye, namely the choroid and the retina, are quiescent in normal adult eye. DR starts with the damage to the small vessels in the retina. Decreased flow causes hypoxia and increases vascular endothelial growth factor (VEGF), causing inappropriate neovascularization and vascular leakage, whereas aberrant capillaries to invade the retina and the vitreous humor (proliferative retinopathy) leading to hemorrhage, scarring, and detachment. The compositions and methods of the present invention may be used to treat such conditions.

VEGF is one of the most prevalent angiogenic growth factors, responsible for pathological angiogenesis in cancer and in eye disease, including acute macular degeneration (AMD, wet type), diabetic retinopathy (DR) and retinopathy of prematurity (ROP). PEDF depletion makes cornea, vireous, retina, and choroid permissive for angiogenesis. In contrast to VEGF, PEDF remains high in normoxia and decreases in low $O_2$. Animal models of DR, ROP and AMD reveal that neovascularization in adult eye is determined by the ratio between pro-angiogenic VEGF and anti-angiogenic PEDF. Purified, adenoviral and lentiviral PEDF are effective against neovascularization in animal models of DR and AMD.

The PEDF gene is mapped to 17p13, a locus frequently lost in primitive tumors of the CNS and in some ovarian tumors where PEDF is a candidate tumor suppressor. Genome analysis of mouse B16 melanoma and normal skin reveals frequent allelic loss of PEDF indicating a link between PEDF, melanoma and angiogenesis. PEDF treatment inhibits the growth of endometrial carcinoma cells. PEDF secretion is low in senescent endometrial fibroblasts, a decrease that may contribute to the age-related increase in cancer incidence by creating permissive environment for the endometrial tumors.

Crawford and co-workers showed that PEDF from Schwann cells differentiates adjacent neuroblastoma tumors and acts as a multifunctional anti-tumor agent, by (a) inhibiting angiogenesis and (b) expanding Schwannian and differentiated components the tumor, creating a feedback loop that limits or reverses tumor growth. PEDF gene transfer of inhibits tumor growth of thoracic malignancies, melanoma and hepatocellular carcinoma in syngeneic murine models.

PEDF belongs to the sub-family of inactive serpins (serine protease inhibitors), serpin reactive loop contributes neither to angioinhibitory nor to neurotropic function. PEDF acts against wide variety of angiogenic stimuli by inducing apoptosis in the activated endothelial cells via a cascade where CD95L, a death ligand is upregulated by PEDF itself and CD95/Fas death receptor is increased by angiogenic stimuli. In addition, PEDF blocks cFLIP, an endogenous caspase inhibitor.

In contrast, PEDF induces survival of the neural crest cells and photoreceptors. The region responsible for this neurotrophic function has been mapped to a 44-mer peptide (positions 58-101). PEDF neuroprotective function requires the activation of NF-κB transcription factor and reverses the decrease in Bcl-2 in pericytes exposed to advanced glycation end product (AGE).

PEDF is a 50 kDa glycoprotein. Numerous investigations have shed light on the structure-function relationships of this molecule (FIG. 1). It binds to collagen and heparin, through nonoverlapping regions (collagen binding may be required for PEDF antiangiogenic activity). PEDF C-terminal fragment (amino acids 195-400) does not reproduce the effects on self-renewal, angiogenesis or neuroprotection. The antiangiogenic and neurotrophic activities are located in the N-terminal portion of the molecule, in two sites. One anti-angiogenic region is clearly distinct the neurotrophic epitope, it is a 34-amino acid (residues 44-77). The other anti-angiogenic region is a small subdomain of the 44-mer, which acid region that can mediate neurotrophic actions (amino acids 78-121). As a 44-mer this region is not anti-angiogenic, however a smaller fragment (ERT, residues 78-121) retains both neurotrophic and angiogenic activity. The present invention is not limited to a particular mechanism. Nonetheless, taken together, the existing data support a model in which binding of PEDF to extracellular matrix (collagen) regulates the exposure of molecular domains, and thus determine its neurotrophic or antiangiogenic activities. In support of the notion that allosteric modulation of PEDF can regulate its biological activity, phosphorylation of residues 24 and 114 by casein kinase 2 (CK2) can enhance the antiangiogenic functions and decrease neurotrophic activity. Conversely, phosphorylation at residue 227 by PKA decreases the antiangiogenic activity.

The combination of neuroprotective and antiangiogenic properties makes PEDF and active fragments thereof valuable agents in diseases and disorders where neurovascular interactions go haywire, such as brain tumors or macular degeneration; in the latter, choroidal blood vessels invade the delicate retinal macula, destroying high-acuity central vision in their wake and leaving approximately half a million people in the US legally blind. The compositions and methods of the present invention may be employed to treat such conditions.

PEDF further finds use in the treatment of highly vascular cancer types (e.g., breast cancer, ovarian cancer), highly metastatic cancer types (e.g., melanoma) and ocular disease (e.g., diabetic retinopathy, retinopathy of prematurity, and acute macular degeneration (wet type)). The compositions and methods of the present invention may be used to treat such conditions.

Experiments conducted during the course of development of embodiments of the present invention included fine mapping of anti-angiogoenic activity of the Pigment Epithelial-derived Factor, PEDF, using a 34-mer PEDF peptide (amino acids 44-77 at the N-terminus). It was demonstrated that an 18-mer fragment of PEDF effectively blocks VEGF-induced angiogenesis in vitro and in vivo in the subcutaneous matrigel plug assays.

This shorter PEDF fragment is more active in blocking angiogenesis than the original 34-mer. Accordingly, in some embodiments, the present invention provides PEDF peptides (e.g., the 18-mer; SEQ ID NO:2), or other short peptides (e.g., SEQ ID NOs: 3-49) for the treatment of the above and other angiogenesis-dependent disease. In certain embodiments, the peptide is selected from an amino acid sequence represented by SEQ ID NOs: 2, 12, 13, 22, 23, 33, 34, 41-49, 52, 53, 62, 63, 73, 74, 84, 85, and 92-100. In other embodiments, the peptide is selected from an amino acid sequence represented by SEQ ID NOs:1-49 and 52-100.

II. Therapeutic Applications

In some embodiments, the present invention provides therapies for angiogenic (e.g., cancer and ocular diseases) and neurovascular related diseases. In some embodiments, therapies provide PEDF peptides (e.g., SEQ ID NO:1-49 or 52-100) for the treatment of angiogenic and neurovascular related diseases.

A. Administering Chemotherapeutics Comprising PEDF and/or PEDF Peptides

It is contemplated that PEDF, PEDF-derived peptides (e.g., SEQ ID NO:1-49 or 52-100), and PEDF-derived peptide analogues or mimetics, can be administered systemically or locally to inhibit tumor cell proliferation and angiogenesis, and induce tumor cell death in cancer patients. They can be administered intravenously, intrathecally, intraperitoneally as well as orally. Moreover, they can be administered alone or in combination with anti-proliferative drugs.

i. PEDF Peptides

The present invention is not limited to a particular PEDF derived peptide. In some embodiments, the 18 amino acid peptide described by SEQ ID NO:2 or 52 is utilized. In other embodiments, shorter (e.g., 13, 14, 15, 16, or 17) amino acid peptides may be utilized. For example, exemplary peptides include, but are not limited to, a peptide comprising or consisting of one of the following sequences:

```
DLYRVRSSTSPTTN;          (SEQ ID NO: 1)
NFGYDLYRVRSSTSPTTN;      (SEQ ID NO: 2)
FGYDLYRVRSSTSPTTN;       (SEQ ID NO: 4)
GYDLYRVRSSTSPTTN;        (SEQ ID NO: 5)
YDLYRVRSSTSPTTN;         (SEQ ID NO: 6)
NFGYDLYRVRSSTSPTT;       (SEQ ID NO: 7)
NFGYDLYRVRSSTSPT;        (SEQ ID NO: 8)
NFGYDLYRVRSSTSP;         (SEQ ID NO: 9)
NFGYDLYRVRSSTS;          (SEQ ID NO: 10)
or
NFGYDLYRVRSST.           (SEQ ID NO: 11)
```

In other embodiments, peptides longer than the 18-mer shown in SEQ ID NO:2 (NFGYDLYRVRSSTSPTTN) are employed. For example, exemplary peptides include, but are not limited to a peptide comprising or consisting of one of the following sequences:

```
                                         (SEQ ID NO: 12)
SNFGYDLYRVRSSTSPTTN;

(SEQ ID NO: 13)
VSNFGYDLYRVRSSTSPTTN;

(SEQ ID NO: 14)
AVSNFGYDLYRVRSSTSPTTN;

(SEQ ID NO: 15)
AAVSNFGYDLYRVRSSTSPTTN;

(SEQ ID NO: 3)
AAAVSNFGYDLYRVRSSTSPTTN;

(SEQ ID NO: 16)
LAAAVSNFGYDLYRVRSSTSPTTN;

(SEQ ID NO: 17)
KLAAAVSNFGYDLYRVRSSTSPTTN;

(SEQ ID NO: 18)
NKLAAAVSNFGYDLYRVRSSTSPTTN;

(SEQ ID NO: 19)
VNKLAAAVSNFGYDLYRVRSSTSPTTN;

(SEQ ID NO: 20)
PVNKLAAAVSNFGYDLYRVRSSTSPTTN;

(SEQ ID NO: 21)
VPVNKLAAAVSNFGYDLYRVRSSTSPTTN;

(SEQ ID NO: 22)
NFGYDLYRVRSSTSPTTNV;

(SEQ ID NO: 23)
NFGYDLYRVRSSTSPTTNVL;

(SEQ ID NO: 24)
NFGYDLYRVRSSTSPTTNVLL;

(SEQ ID NO: 25)
NFGYDLYRVRSSTSPTTNVLLS;

(SEQ ID NO: 26)
NFGYDLYRVRSSTSPTTNVLLSP;

(SEQ ID NO: 27)
NFGYDLYRVRSSTSPTTNVLLSPL;
```

```
NFGYDLYRVRSSTSPTTNVLLSPLS;            (SEQ ID NO: 28)

NFGYDLYRVRSSTSPTTNVLLSPLSV;           (SEQ ID NO: 29)

NFGYDLYRVRSSTSPTTNVLLSPLSVA;          (SEQ ID NO: 30)

NFGYDLYRVRSSTSPTTNVLLSPLSVAT;         (SEQ ID NO: 31)

NFGYDLYRVRSSTSPTTNVLLSPLSVATA;        (SEQ ID NO: 32)

SNFGYDLYRVRSSTSPTTNV;                 (SEQ ID NO: 33)

VSNFGYDLYRVRSSTSPTTNVL;               (SEQ ID NO: 34)

AVSNFGYDLYRVRSSTSPTTNVLL;             (SEQ ID NO: 35)

AAVSNFGYDLYRVRSSTSPTTNVLLS;           (SEQ ID NO: 36)

AAAVSNFGYDLYRVRSSTSPTTNVLLSP;         (SEQ ID NO: 37)

LAAAVSNFGYDLYRVRSSTSPTTNVLLSPL;       (SEQ ID NO: 38)

KLAAAVSNFGYDLYRVRSSTSPTTNVLLSPLS;     (SEQ ID NO: 39)

NKLAAAVSNFGYDLYRVRSSTSPTTNVLLSPLSV;   (SEQ ID NO: 40)

SNFGYDLYRVRSSTSPTTNVL;                (SEQ ID NO: 41)

VSNFGYDLYRVRSSTSPTTNV;                (SEQ ID NO: 42)

XNFGYDLYRVRSSTSPTTN;                  (SEQ ID NO: 43)

XXNFGYDLYRVRSSTSPTTN;                 (SEQ ID NO: 44)

NFGYDLYRVRSSTSPTTNX;                  (SEQ ID NO: 45)

NFGYDLYRVRSSTSPTTNXX;                 (SEQ ID NO: 46)

XNFGYDLYRVRSSTSPTTNX;                 (SEQ ID NO: 47)

XNFGYDLYRVRSSTSPTTNXX;                (SEQ ID NO: 48)
or

XXNFGYDLYRVRSSTSPTTNXX.               (SEQ ID NO: 49)
```

In the above sequences, "X" stands for any amino acid, including modified amino acids.

Peptides that are longer or short than SEQ ID NO:2 can be designed based on a PEDF sequence (e.g., SEQ ID NO:50 or 101) shown in FIGS. 7 and 10 respectively (e.g., by adding or deleting amino acids from either end of SEQ ID NO:2 or 52).

In other embodiments, other PEDF peptides are employed (e.g., that replace a "T" with an "M" at position 13 in SEQ ID NO:2).

```
DLYRVRSSMSPTTN;                       (SEQ ID NO: 52)

NFGYDLYRVRSSMSPTTN;                   (SEQ ID NO: 53)

FGYDLYRVRSSMSPTTN;                    (SEQ ID NO: 54)

GYDLYRVRSSMSPTTN;                     (SEQ ID NO: 55)

YDLYRVRSSMSPTTN;                      (SEQ ID NO: 56)

NFGYDLYRVRSSMSPTT;                    (SEQ ID NO: 57)

NFGYDLYRVRSSMSPT;                     (SEQ ID NO: 58)

NFGYDLYRVRSSMSP;                      (SEQ ID NO: 59)

NFGYDLYRVRSSMS;                       (SEQ ID NO: 60)

NFGYDLYRVRSSM;                        (SEQ ID NO: 61)

SNFGYDLYRVRSSMSPTTN;                  (SEQ ID NO: 62)

VSNFGYDLYRVRSSMSPTTN;                 (SEQ ID NO: 63)

AVSNFGYDLYRVRSSMSPTTN;                (SEQ ID NO: 64)

AAVSNFGYDLYRVRSSMSPTTN;               (SEQ ID NO: 65)

AAAVSNFGYDLYRVRSSMSPTTN;              (SEQ ID NO: 66)

LAAAVSNFGYDLYRVRSSMSPTTN;             (SEQ ID NO: 67)

KLAAAVSNFGYDLYRVRSSMSPTTN;            (SEQ ID NO: 68)

NKLAAAVSNFGYDLYRVRSSMSPTTN;           (SEQ ID NO: 69)

VNKLAAAVSNFGYDLYRVRSSMSPTTN;          (SEQ ID NO: 70)

PVNKLAAAVSNFGYDLYRVRSSMSPTTN;         (SEQ ID NO: 71)

VPVNKLAAAVSNFGYDLYRVRSSMSPTTN;        (SEQ ID NO: 72)

NFGYDLYRVRSSMSPTTNV;                  (SEQ ID NO: 73)

NFGYDLYRVRSSMSPTTNVL;                 (SEQ ID NO: 74)

NFGYDLYRVRSSMSPTTNVLL;                (SEQ ID NO: 75)

NFGYDLYRVRSSMSPTTNVLLS;               (SEQ ID NO: 76)

NFGYDLYRVRSSMSPTTNVLLSP;              (SEQ ID NO: 77)

NFGYDLYRVRSSMSPTTNVLLSPL;             (SEQ ID NO: 78)
```

NFGYDLYRVRSSMSPTTNVLLSPLS; (SEQ ID NO: 79)

NFGYDLYRVRSSMSPTTNVLLSPLSV; (SEQ ID NO: 80)

NFGYDLYRVRSSMSPTTNVLLSPLSVA; (SEQ ID NO: 81)

NFGYDLYRVRSSMSPTTNVLLSPLSVAT; (SEQ ID NO: 82)

NFGYDLYRVRSSMSPTTNVLLSPLSVATA; (SEQ ID NO: 83)

SNFGYDLYRVRSSMSPTTNV; (SEQ ID NO: 84)

VSNFGYDLYRVRSSMSPTTNVL; (SEQ ID NO: 85)

AVSNFGYDLYRVRSSMSPTTNVLL; (SEQ ID NO: 86)

AAVSNFGYDLYRVRSSMSPTTNVLLS; (SEQ ID NO: 87)

AAAVSNFGYDLYRVRSSMSPTTNVLLSP; (SEQ ID NO: 88)

LAAAVSNFGYDLYRVRSSMSPTTNVLLSPL; (SEQ ID NO: 89)

KLAAAVSNFGYDLYRVRSSMSPTTNVLLSPLS; (SEQ ID NO: 90)

NKLAAAVSNFGYDLYRVRSSMSPTTNVLLSPLSV; (SEQ ID NO: 91)

SNFGYDLYRVRSSMSPTTNVL; (SEQ ID NO: 92)

VSNFGYDLYRVRSSMSPTTNV; (SEQ ID NO: 93)

XNFGYDLYRVRSSMSPTTN; (SEQ ID NO: 94)

XXNFGYDLYRVRSSMSPTTN; (SEQ ID NO: 95)

NFGYDLYRVRSSMSPTTNX; (SEQ ID NO: 96)

NFGYDLYRVRSSMSPTTNXX; (SEQ ID NO: 97)

XNFGYDLYRVRSSMSPTTNX; (SEQ ID NO: 98)

XNFGYDLYRVRSSMSPTTNXX; (SEQ ID NO: 99)
or

XXNFGYDLYRVRSSMSPTTNXX. (SEQ ID NO: 100)

In the above sequences, "X" stands for any amino acid, including modified amino acids.

The PEDF peptides may be obtained using any suitable method. For example, in some embodiments, peptides are produced recombinantly in host cells. Thus, for example, a polypeptide encoding the desired PEDF peptides may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In some embodiments of the present invention, the constructs comprise a vector, such as a plasmid or viral vector, into which a sequence encoding a PEDF peptide has been inserted, in a forward or reverse orientation. In still other embodiments, the sequence is assembled in appropriate phase with translation initiation and termination sequences. In some embodiments, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE 9 (Qiagen), pBS, pD10, phagescript, psiX174, pbluescript SK, pBSKS, pNH8A, pNH16a, pNH18A, pNH46A (Stratagene); ptrc99a, pKK223 3, pKK233 3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non transcribed sequences. In other embodiments, DNA sequences derived from the SV40 splice, and polyadenylation sites may be used to provide the required non transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis acting elements of DNA, usually about from 10 to 300 by that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In some embodiments, peptides are expressed in host cells. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe*, Drosophila S2 cells, Spodoptera Sf9 cells, Chinese hamster ovary (CHO) cells, COS 7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by transfection or electroporation (See e.g., Davis et al., Basic Methods in Molecular Biology, [1986]). Alternatively, in some embodiments of the present invention, the polypeptides of the invention can be synthetically produced by conventional peptide synthesizers.

Peptides can be expressed in mammalian cells, yeast, bacteria, or other cells under the control of appropriate promoters. Cell free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze thaw cycling, sonication, mechanical disruption, or use of cell lysing agents.

Peptides may be recovered and purified from host cells, using any suitable method include, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments of the present invention, high performance liquid chromatography (HPLC) is employed for purification steps.

In an alternate embodiment of the invention, nucleic acid sequence encoding the peptides are synthesized, whole or in part, using chemical methods well known in the art (See e.g., Caruthers et al., Nucl. Acids Res. Symp. Ser., 7:215 233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 2817 [1981]). In other embodiments of the present invention, the peptide is produced using chemical methods. For example, peptides can be synthesized by solid phase techniques, cleaved from the resin, and purified by preparative high performance liquid chromatography (See e.g., Creighton, Proteins Structures And Molecular Principles, W H Freeman and Co, New York N.Y. [1983]). In some embodiments of the present invention, the composition of the synthetic peptides is confirmed by amino acid analysis or sequencing (See e.g., Creighton, supra).

Direct peptide synthesis can be performed using various solid phase techniques (Roberge et al., Science 269:202 204 [1995]) and automated synthesis may be achieved, for example, using ABI 431A Peptide Synthesizer (Perkin Elmer) in accordance with the instructions provided by the manufacturer.

ii. Preparations and Administration

Where combinations are contemplated, it is not intended that the present invention be limited by the particular nature of the combination. The present invention contemplates combinations as simple mixtures as well as chemical hybrids. An example of the latter is where the peptide or drug is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

B. Designing Mimetics

It may be desirable to administer an analogue of a PEDF-derived peptide (e.g., an analogue of SEQ ID NO:2 or SEQ ID NO:52). A variety of designs for such mimetics are possible. For example, cyclic peptides, in which the necessary conformation for binding is stabilized by nonpeptides, are specifically contemplated. (See, e.g., U.S. Pat. No. 5,192,746 to Lobl et al., U.S. Pat. No. 5,169,862 to Burke, Jr. et al., U.S. Pat. No. 5,539,085 to Bischoff et al., U.S. Pat. No. 5,576,423 to Aversa et al., U.S. Pat. No. 5,051,448 to Shashoua, and U.S. Pat. No. 5,559,103 to Gaeta et al., all hereby incorporated by reference, describe multiple methods for creating such compounds.

Synthesis of nonpeptide compounds that mimic peptide sequences is also known in the art. For example, Eldred et al., J. Med. Chem. 37:3882 (1994), describe nonpeptide antagonists that mimic the Arg-Gly-Asp sequence. Likewise, Ku et al., J. Med. Chem. 38:9 (1995) give further elucidation of the synthesis of a series of such compounds. Such nonpeptide compounds are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexyl-carbodiimide (DCC). The attack of a free amino group on the activated carboxyl leads to the formation of a peptide bond and the release of dicyclohexylurea. It may be important to protect potentially reactive groups other than the amino and carboxyl groups intended to react. For example, the (x-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

The methods of the present invention can be practiced in vitro or in vivo.

For example, the method of the present invention can be used in vitro to screen for compounds which are potentially useful for combinatorial use with PEDF peptides (e.g., SEQ ID NOs: 1-49 or 52-100) for treating cancer or other angiogenic or neurovascular diseases; to evaluate a compound's efficacy in treating cancer; or to investigate the mechanism by which a compound combats cancer or other angiogenic or neurovascular diseases (e.g., whether it does so by inducing apoptosis, by inducing differentiation, by decreasing proliferation, etc). For example, once a compound has been identified as a compound that works in combination with PEDF peptides to inhibit angiogenesis, proliferation and/or cause apoptosis of cancer cells, one skilled in the art can apply the method of the present invention in vitro to evaluate the degree to which the compound induces apoptosis and/or decreases angiogenesis, proliferation of cancer cells; or one skilled in the art can apply the method of the present invention to determine whether the compound operates by inducing apoptosis, by decreasing proliferation and/or angiogenesis, or by a combination of these methods.

Alternatively, the method of the present invention can be used in vivo to treat cancers, (e.g., including, but not limited to, ovarian cancer, breast cancer) or other angiogenic or neurovascular diseases. In the case where the method of the present invention is carried out in vivo, for example, where the cancer cells are present in a human subject, contacting can be carried out by administering a therapeutically effective amount of the compound to the human subject (e.g., by directly injecting the compound into a tumor or through systemic administration).

The present invention, in another aspect thereof, relates to a method of treating cancer or other angiogenic or neurovascular diseases. The method includes administering to the subject an amount of a compound effective to inhibit angiogenesis, proliferation and/or cause the death of cancer cells.

Suitable subjects include, for example mammals, such as rats, mice, cats, dogs, monkeys, and humans. Suitable human subjects include, for example, those which have previously been determined to be at risk of having cancer or other angiogenic or neurovascular diseases and those who have been diagnosed as having cancer or other angiogenic or neurovascular diseases.

In subjects who are determined to be at risk of having cancer, the compositions of the present invention are administered to the subject preferably under conditions effective to decrease angiogenesis, proliferation and/or induce apoptosis of the cancer cells in the event that they develop.

The compositions herein may be made up in any suitable form appropriate for the desired use. Examples of suitable dosage forms include oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In addition to PEDF peptides (e.g., SEQ ID NOs: 1-49 or 52-100), these compositions can include other active materials, particularly, actives which have been identified as useful in the treatment of cancers (e.g., adenocarcinomas). These actives can be broad-based anti-cancer agents, such that they also are useful in treating more than one type of cancer or they may be more specific (e.g., in a case where the other active material is useful for treating adenocarcinomas but not useful for treating oral squamous cell carcinoma). The other actives can also have non-anti-cancer pharmacological properties in addition to their anti-cancer properties. For example, the other actives can have anti-inflammatory properties, or, alternatively, they can have no such anti-inflammatory properties.

It will be appreciated that the actual preferred amount of composition comprising PEDF peptide to be administered according to the present invention may vary according to the particular composition formulated, and the mode of administration. Many factors that may modify the action of the compositions (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

C. Therapeutic Agents Combined or Co-Administered with PEDF Peptides

A wide range of therapeutic agents find use with the present invention. For example, any therapeutic agent that can be co-administered with PEDF peptides (e.g., SEQ ID NOs:1-49 or 52-100), or associated with PEDF is suitable for use in the present invention.

In some embodiments, PEDF peptides described herein (e.g., SEQ ID NO:2 or 52) are administered in combination with the ERT 44-mer fragment, ERT of PEDF.

Some embodiments of the present invention provide administering to a subject an effective amount of PEDF peptides (and enantiomers, derivatives, and pharmaceutically acceptable salts thereof) and at least one anticancer agent (e.g., a conventional anticancer agent, such as, chemotherapeutic drugs, and/or radiation therapy).

Anticancer agent mechanisms suitable for use with the present invention include, but are not limited to, agents that induce apoptosis, agents that induce/cause nucleic acid damage, agents that inhibit nucleic acid synthesis, agents that affect microtubule formation, and agents that affect protein synthesis or stability.

Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel (Taxol), and Docetaxel, etc.), and chromatin function inhibitors, including, topoisomerase inhibitors, such as, epipodophyllotoxins (e.g., Etoposide (VP-16), and Teniposide (VM-26), etc.), and agents that target topoisomerase I (e.g., Camptothecin and Isirinotecan (CPT-11), etc.); 2) covalent DNA-binding agents (alkylating agents), including, nitrogen mustards (e.g., Mechlorethamine, Chlorambucil, Cyclophosphamide, Ifosphamide, and Busulfan (Mylepan), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents (antitumor antibiotics), including, nucleic acid inhibitors (e.g., Dactinomycin (Actinomycin D), etc.), anthracyclines (e.g., Daunorubicin (Daunomycin, and Cerubidine), Doxorubicin (Adriamycin), and Idarubicin (Idamycin), etc.), anthracenediones (e.g., anthracycline analogues, such as, (Mitoxantrone), etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines (e.g., 5-fluorouracil (Adrucil), 5-fluorodeoxyuridine (FdUrd) (Floxuridine)) etc.), and cytosine arabinosides (e.g., Cytosar (ara-C) and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole (Arimidex), etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons (e.g., IFN-γ, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) other inhibitors of angiogenesis.

In preferred embodiments, the present invention provides administration of an effective amount of PEDF peptides and at least one conventional anticancer agent that induces apoptosis and/or prevents cancer cell proliferation to a subject. In some preferred embodiments, the subject has a disease characterized by metastasis. In yet other preferred embodiments, the present invention provides administration of an effective amount of PEDF peptides and a taxane (e.g., Docetaxel) to a subject having a disease characterized by the overexpression of Bcl-2 family protein(s) (e.g., Bcl-2 and/or Bcl-$X_L$).

The taxanes (e.g., Docetaxel) are an effective class of anticancer chemotherapeutic agents. (See e.g., K. D. Miller and G. W. Sledge, Jr. Cancer Investigation, 17:121-136 (1999)). While the present invention is not intended to be limited to any particular mechanism, taxane-mediated cell death is though to proceed through intercellular microtubule stabilization and subsequent induction of the apoptotic pathway. (See e.g., S. Haldar et al., Cancer Research, 57:229-233 (1997)).

In some other embodiments, cisplatin and taxol are specifically contemplated for use with the PEDF peptide compositions of the present invention. Cisplatin and Taxol have a well-defined action of inducing apoptosis in tumor cells (See e.g., Lanni et al., Proc. Natl. Acad. Sci., 94:9679 (1997); Tortora et al., Cancer Research 57:5107 (1997); and Zaffaroni et al., Brit. J. Cancer 77:1378 (1998)). However, treatment with these and other chemotherapeutic agents is difficult to accomplish without incurring significant toxicity. The agents currently in use are generally poorly water soluble, quite toxic, and given at doses that affect normal cells as wells as diseased cells. For example, paclitaxel (Taxol), one of the most promising anticancer compounds discovered, is poorly soluble in water. Paclitaxel has shown excellent antitumor activity in a wide variety of tumor models such as the B 16 melanoma, L1210 leukemias, MX-1 mammary tumors, and CS-1 colon tumor xenografts. However, the poor aqueous solubility of paclitaxel presents a problem for human administration. Accordingly, currently used paclitaxel formulations require a cremaphor to solubilize the drug. The human clinical dose range is 200-500 mg. This dose is dissolved in a 1:1 solution of ethanol:cremaphor and diluted to one liter of fluid given intravenously. The cremaphor currently used is polyethoxylated castor oil. It is given by infusion by dissolving in the cremaphor mixture and diluting with large volumes of an aqueous vehicle. Direct administration (e.g., subcutaneous) results in local toxicity and low levels of activity.

Any pharmaceutical that is routinely used in a cancer therapy context finds use in the present invention. Conventional anticancer agents that are suitable for administration with the disclosed PEDF peptide compositions include, but are mot limited to, adriamycin, 5-fluorouracil, etoposide, camptothecin, methotrexate, actinomycin-D, mitomycin C, or more preferably, cisplatin. These agent may be prepared and used as a combined therapeutic composition, or kit, by combining it with an immunotherapeutic agent, as described herein.

In some embodiments of the present invention, the therapeutic PEDF treatments further comprise one or more agents that directly cross-link nucleic acids (e.g., DNA) to facilitate DNA damage leading to a synergistic, antineoplastic agents of the present invention. For example, agents such as cisplatin, and other DNA alkylating agents may be used. Cisplatin has been widely used to treat cancer, with efficacious doses used in clinical applications of 20 mg/M$^2$ for 5 days every three weeks for a total of three courses. The compositions of the present invention may be delivered via any suitable method, including, but not limited to, injection intravenously, subcutaneously, intratumorally, intraperitoneally, or topically (e.g., to mucosal surfaces).

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are administered through bolus injections intravenously at doses ranging from 25-75 M/$^2$ at 21 day intervals for adriamycin, to 35-50 Mg/M$^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

In preferred embodiments, the anticancer agents (e.g., antiangiogenic factors discussed herein) used in the present invention are those that are amenable to co-administration with PEDF peptides or are otherwise associated with the PEDF peptides such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anticancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

In some embodiments, the drugs are attached to PEDF with photocleavable linkers. For example, several heterobifunctional, photocleavable linkers that find use with the present invention are described (See, e.g., Ottl et al., Bioconjugate Chem., 9:143 (1998)). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In an exemplary embodiment, an active group of a PEDF peptide is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). Thus conjugated, the drug is inactive and will not harm normal cells. When the conjugate is localized within tumor cells, it is exposed to laser light of the appropriate near-UV wavelength, causing the active drug to be released into the cell.

An alternative to photocleavable linkers are enzyme cleavable linkers. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 (1999)). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly may be used.

The present invention is not limited by the nature of the therapeutic technique. For example, other conjugates that find use with the present invention include, but are not limited to, using conjugated boron dusters for BNCT (See, e.g., Capala et al., Bioconjugate Chem., 7:7 (1996)), the use of radioisotopes, and conjugation of toxins such as ricin.

Antimicrobial therapeutic agents may also be used in combination with PEDF peptides as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins, antisense nucleic acids, membrane disruptive agents and the like, used alone or in combination. Indeed, any type of antibiotic may be used including, but not limited to, antibacterial agents, anti-viral agents, anti-fungal agents, and the like.

In still further embodiments, another component of the present invention is that the PEDF peptide be associated with targeting agents (PEDF peptide-targeting agent complex) that are able to specifically target a particular cell type (e.g., tumor cell). Generally, the PEDF peptide that is associated with a targeting agent, targets neoplastic cells through interaction of the targeting agent with a cell surface moiety and is taken into the cell through receptor mediated endocytosis.

Any moiety known to be located on the surface of target cells (e.g., tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

In some embodiments of the present invention, the targeting moiety may also function as an agent to identify a particular tumor characterized by expressing a receptor that the targeting agent (ligand) binds with, for example, tumor specific antigens including, but not limited to, carcinoembryonic antigen, prostate specific antigen, tyrosinase, ras, a sialyly lewis antigen, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary find use with the present invention. Alternatively the targeting moiety may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pancarcinoma antigen, ovarian carcinoma antigen (CA125), prostate specific antigen, melanoma antigen gp75, CD9, CD63, CD53, CD37, R2, CD81, CO029, TI-1, L6 and SAS. Of course these are merely exemplary tumor suppressors and it is envisioned that the present invention may be used in conjunction with any other agent that is or becomes known to those of skill in the art as a tumor suppressor.

In preferred embodiments of the present invention, targeting is directed to factors expressed by an oncogene (e.g., bcl-2 and/or bcl-$X_L$). These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Receptors and their related ligands that find use in the context of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the targeting aspect of the present invention include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, .alpha.-endorphin, .alpha. melanocyte stimulating hormone, cholecystokinin, endothelin I, galanin, gastric inhibitory peptide (GIP), glucagon, insulin, amylin, lipotropins, GLP-1 (7-37) neurophysins, and somatostatin.

In addition, the present invention contemplates that vitamins (both fat soluble and non-fat soluble vitamins) used as targeting agents may be used to target cells that have receptors for, or otherwise take up these vitamins. Particularly preferred for this aspect are the fat soluble vitamins, such as vitamin D and its analogues, vitamin E, Vitamin A, and the like or water soluble vitamins such as Vitamin C, and the like.

In some embodiments of the present invention, any number of cancer cell targeting groups are associated with PEDF peptides (e.g., SEQ ID NOs:1-49 or 52-100). Thus, PEDF peptides associated with targeting groups are specific for targeting cancer cells (i.e., much more likely to attach to cancer cells and not to healthy cells).

In preferred embodiments of the present invention, targeting groups are associated (e.g., covalently or noncovalently bound) to PEDF peptides with either short (e.g., direct coupling), medium (e.g., using small-molecule bifunctional linkers such as SPDP, sold by Pierce Chemical Company), or long (e.g., PEG bifunctional linkers, sold by Shearwater Polymers) linkages.

In preferred embodiments of the present invention, the targeting agent is an antibody or antigen binding fragment of an antibody (e.g., Fab units). For example, a well-studied antigen found on the surface of many cancers (including breast HER2 tumors) is glycoprotein p185, which is exclusively expressed in malignant cells (Press et al., Oncogene 5:953 (1990)). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegrarn et al., Proc. Am. Soc. Clin. Oncol., 14:106 (1995)). Park et al. have attached Fab fragments of rhuMabHER2 to small unilamellar liposomes, which then can be loaded with the chemotherapeutic doxorubicin (dox) and targeted to HER2 overexpressing tumor xenografts (Park et al., Cancer Lett., 118:153 (1997) and Kirpotin et al., Biochem., 36:66 (1997)). These dox-loaded "immunoliposomes" showed increased cytotoxicity against tumors compared to corresponding non-targeted dox-loaded liposomes or free dox, and decreased systemic toxicity compared to free dox.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some preferred embodiments, the antibodies recognize tumor specific epitopes (e.g., TAG-72 (Kjeldsen et al., Cancer Res. 48:2214-2220 (1988); U.S. Pat. Nos. 5,892,020; 5,892, 019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855, 866); Thomsen-Friedenreich (TF) antigen from adenocarcinoma cells (U.S. Pat. No. 5,110,911); "KC-4 antigen" from human prostrate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA)(U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res. 178:271-292 (1988)), MSA breast carcinoma glycoprotein termed (Tjandra et al., Br. J. Surg. 75:811-817 (1988)); MFGM breast carcinoma antigen (Ishida et al., Tumor Biol. 10:12-22 (1989)); DU-PAN-2 pancreatic carcinoma antigen (Lan et al., Cancer Res. 45:305-310 (1985)); CA125 ovarian carcinoma antigen (Hanisch et al., Carbohydr. Res. 178:29-47 (1988)); YH206 lung carcinoma antigen (Hinoda et al., Cancer J., 42:653-658 (1988)). Each of the foregoing references are specifically incorporated herein by reference.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Kohler and Milstein, Nature 256:495-497 (1975)), as well as the trioma technique, the human B-cell hybridoma technique (See e.g., Kozbor et al., Immunol. Today 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)).

According to the invention, techniques described for the production of single chain antibodies (U.S. Pat. No. 4,946,778; herein incorporated by reference) can be adapted to produce specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')$_2$ fragment that can be produced by pepsin digestion of the antibody molecule; the Fab' fragments that can be generated by reducing the disulfide bridges of the F(ab')$_2$ fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

For breast cancer, the cell surface may be targeted with folic acid, EGF, FGF, and antibodies (or antibody fragments) to the tumor-associated antigens MUC1, cMet receptor and CD56 (NCAM).

A very flexible method to identify and select appropriate peptide targeting groups is the phage display technique (See e.g., Cortese et al., Curr. Opin. Biotechol., 6:73 (1995)), which can be conveniently carried out using commercially available kits. The phage display procedure produces a large and diverse combinatorial library of peptides attached to the surface of phage, which are screened against immobilized surface receptors for tight binding. After the tight-binding, viral constructs are isolated and sequenced to identify the peptide sequences. The cycle is repeated using the best peptides as starting points for the next peptide library. Eventually, suitably high-affinity peptides are identified and then screened for biocompatibility and target specificity. In this way, it is possible to produce peptides that can be conjugated to dendrimers, producing multivalent conjugates with high specificity and affinity for the target cell receptors (e.g., tumor cell receptors) or other desired targets.

Related to the targeting approaches described above is the "pretargeting" approach (See e.g., Goodwin and Meares, Cancer (suppl.) 80:2675 (1997)). An example of this strategy involves initial treatment of the patient with conjugates of tumor-specific monoclonal antibodies and streptavidin. Remaining soluble conjugate is removed from the bloodstream with an appropriate biotinylated clearing agent. When the tumor-localized conjugate is all that remains, a gossypol-linked, biotinylated agent is introduced, which in turn localizes at the tumor sites by the strong and specific biotin-streptavidin interaction.

In some embodiments of the present invention, the targeting agents (moities) are preferably nucleic acids (e.g., RNA or DNA). In some embodiments, the nucleic acid targeting moities are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene, 137(1):33-9 (1993)); human nerve growth factor (Binkley et al., Nuc. Acids Res., 23(16):3198-205 (1995)); and vascular endothelial growth factor (Jellinek et al., Biochem., 83(34):10450-6 (1994)). Nucleic acids that bind ligands are preferably identified by the SELEX procedure (See e.g., U.S. Pat. Nos. 5,475,096; 5,270,163; and 5,475,096; and in PCT publications WO 97/38134, WO 98/33941, and WO 99/07724, all of which are herein incorporated by reference), although many methods are known in the art.

EXPERIMENTAL

The following examples are provided in order to demonstrate and further illustrate certain preferred embodiments and aspects of the present invention and are not to be construed as limiting the scope thereof.

EXAMPLE 1

Figure 2:
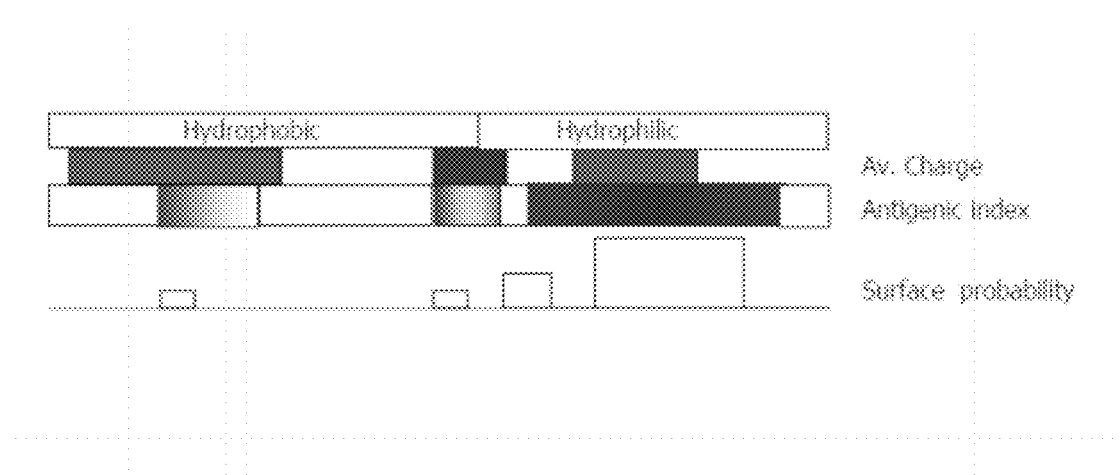
FIG. 2 shows peptide design for the mapping of the 34-mer anti-angiogenic fragments.

This example describes the mapping of a 34-mer peptide of PEDF and the identification of a shorter fragment, the 18-mer, with superior anti-angiogenic characteristics. FIG. 1 shows a schematic representation of identified functional domains of PEDF, including major phosphorylation sites and domains known to be critical for interactions with extracellular matrix. The analysis of the 34-mer structure was performed using Protean software and its hydrophilic profile, antigenic indices and probability of surface exposure were determined. This analysis yielded several candidate peptides to be tested in the in vitro and in vivo angiogenesis assays (FIG. 2).

The C-terminal part of 34-mer is more hydrophilic, with a highly charged area in the middle and high antigenic index and thus is likely to be involved in the interaction with the putative receptor. Three peptides were identified that cover this area as shown in FIG. 2: a shorter 14-amino acid peptide that covers positively charged area with high likelihood of surface exposure (DLYRVRSSTSPTTN; SEQ ID NO:1) and two extended versions, one containing the negatively charged area (NFGY)(NFGYDLYRVRSSTSPTTN; SEQ ID NO:2), and the more extended one, that covers the adjacent neutral stretch (AAAV) (AAAVSNFGYDLYRVRSSTSPTTN; SEQ ID NO:3), which may ensure proper folding. The N-terminal sub-fragment was unlikely to be exposed on the surface of the molecule, and therefore was not tested. Peptide synthesis has been performed to order at BioSource Custom Antibodies and Peptides.

Figure 3:
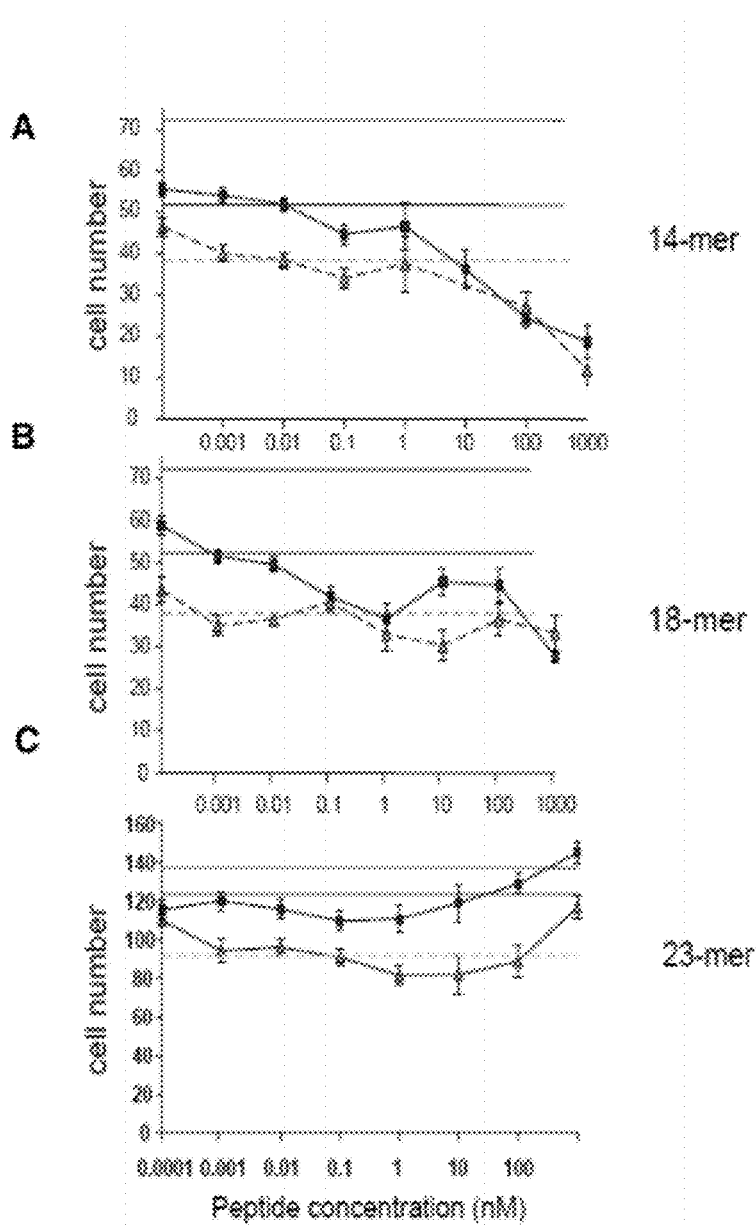
FIG. 3 shows the results of an endothelial cell chemotaxis assay, where endothelial cells traversed a gelatinized microporous membrane up a gradient of bFGF in the absence and the presence of PEDF peptides, including a 14-mer (SEQ ID NO:1.

The initial testing was done in the endothelial cell chemotaxis assay. Human microvascular endothelial cells to traverse gelatinized microporous membrane up the gradient of bFGF was tested in the absence and in the presence of the 14-, 18- and 23-mer peptides (FIG. 3). Human microvascular endothelial cells were plated on the lower side of gelatinized microporous membrane and allowed to adhere. The peptides (14-, 18 and 23-mer) were added at increasing concentrations to the opposite side of the gelatinized microporous membrane (8 μM pores), alone, or in combination with basic fibroblast growth factor (bFGF, 10 ng/ml). The cells migratied to the opposite side of the membrane were counted in 10 high-powered (100×) fields. Every condition was tested in quadruplicate. bFGF-induced chemotaxis is shown (top line in each graph). Basal migration levels (0.1% bovine serum albumin) are indicated with the dotted line. Triangles (Δ) show peptide alone; while squares (■) show peptide with bFGF. The solid line (below the top line mentioned above) indicates the effect of the recombinant human PEDF (rhPEDF) at 20 nM.

The experiments showed that the 14-mer and 18-mer inhibited bFGF-induced migration in a dose-dependent manner. The 23-mer was comparable to PEDF at low concentrations and lost its inhibitory activity at higher doses. The inhibitor activity of the 14-mer and 18-mer were superior to that of native PEDF.

Figure 4:
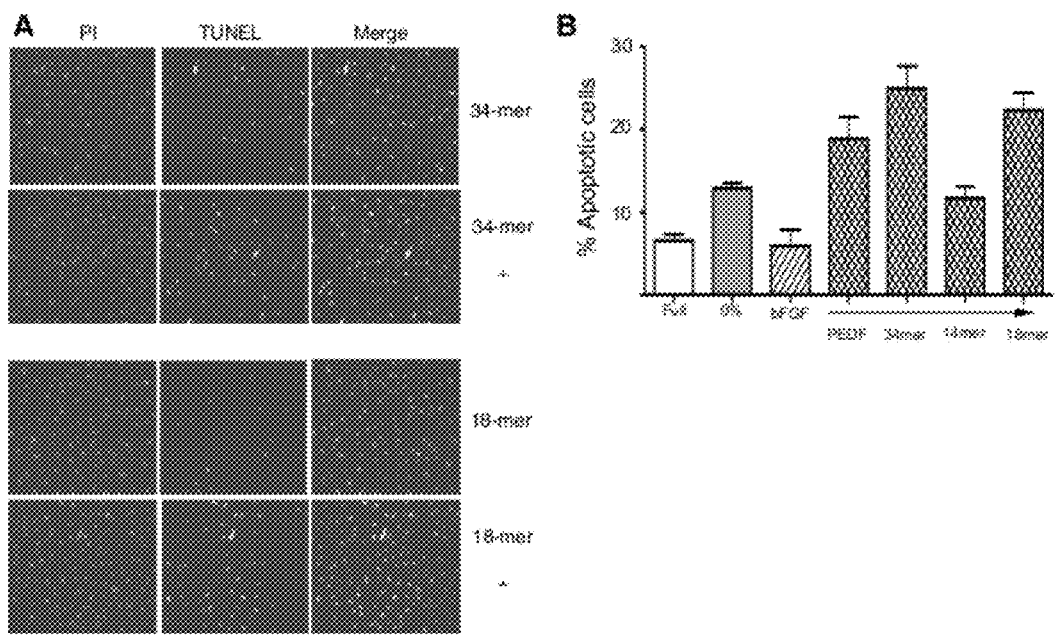
FIG. 4 shows that PEDF peptides block survival effect of bFGF by inducing endothelial cells apoptosis.

The ability of the 34-mer fragments to induce endothelial cell apoptosis was next measured (FIG. 4). The 23-mer failed to induced apoptosis and the 14-mer showed very weak induction of apoptosis. The 18-mer, however, was more potent than the parental PEDF and as potent as the 34-mer in inducing endothelial cell apoptosis.

Figure 5:
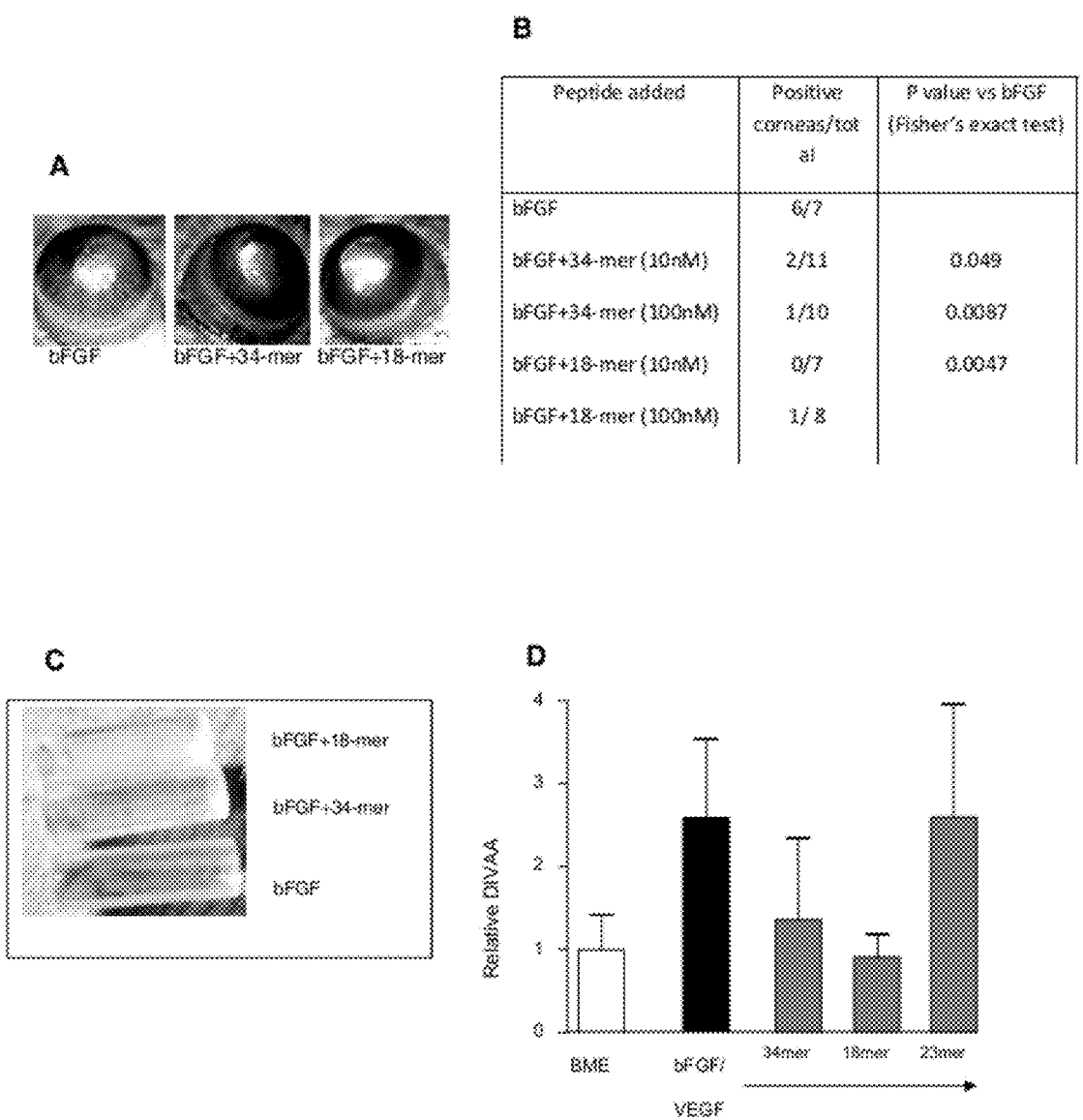
FIG. 5 shows the in vivo anti-angiogenic effect of the PEDF peptides.

Finally, the peptides were tested in vivo, in the corneal angiogenesis and directed in vivo angiogenesis assay (DIVAA). The 34-mer derivatives were compared in vivo with parental PEDF peptide, the 34-mer. FIG. 5 A, B: Corneal angiogenesis assay: the peptides were incorporated with bFGF (50 ng/pellet) into slow-release sucralfate pellets, which were surgically mplanted into the cornea of anesthetized mice, 0.5-1 mm from the vascular limbus. The responses were scored on day 5 post implantation and the ingrowth of blood vessels from the cornea to the pellet was considered a positive response. The responses were scored as positive corneas of total implanted: statistical significance was evaluated with Fisher's Exact test. P<0.05 was considered significant. 5A shows photographs of representative corneas. 5B shows the tabulated results of the cornea assay. 5C, D. DIVAA of the 34-mer and derivative peptides. The peptides were incorporated with a mix of bFGF and VEGF (37.5 and 12.5 ng/ml, respectively) into angioreactors filled with matrigel. The reactors were implanted s.c onto the flanks of the nude mice. On day 7, the reactors were harvested and photographed (5C). Endothelial cells collected from implants by dilution/centrifugation, stained with FITC-lectin and quantified by flow cytometry (5D). In both assays the 18-mer showed the best anti-angiogenic characteristics (FIG. 5). The 23-mer failed to inhibit angiogenesis in the DIVAA assay.

Figure 6:
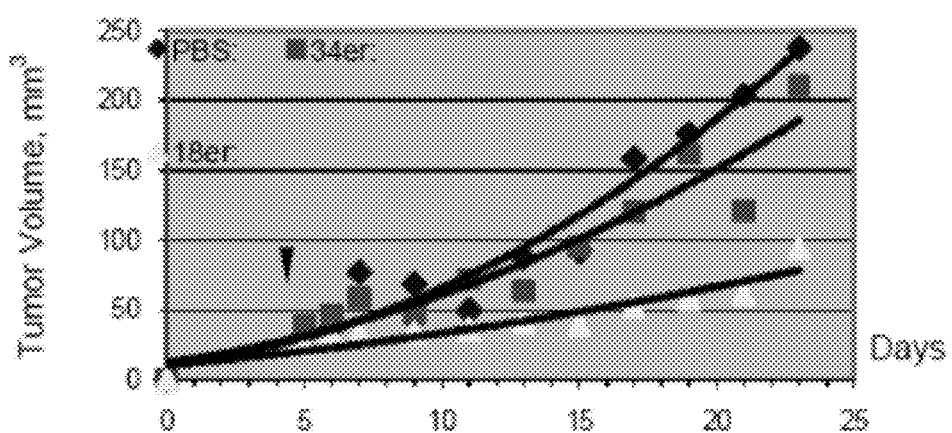
FIG. 6 shows the effects of 34-mer and 18-mer systemic treatment on tumor growth.

When tested in a tumorigenicity assay, the 18-mer significantly inhibited the growth of PC-3 prostate cancer xenografts at 10 mg/kg: synthetic 34-mer had only marginal effect at this dose (FIG. 6). PC-3 cells (2×10$^6$/site) were implanted into hindquarters of nude mice. On day 5 post injection, treatment was commenced with 34-mer and 18-mer (10 mg/kg, i.p.). Note substantial reduction in tumor volume in 18-mer treated tumors (FIG. 6).

EXAMPLE 2

Figure 8:
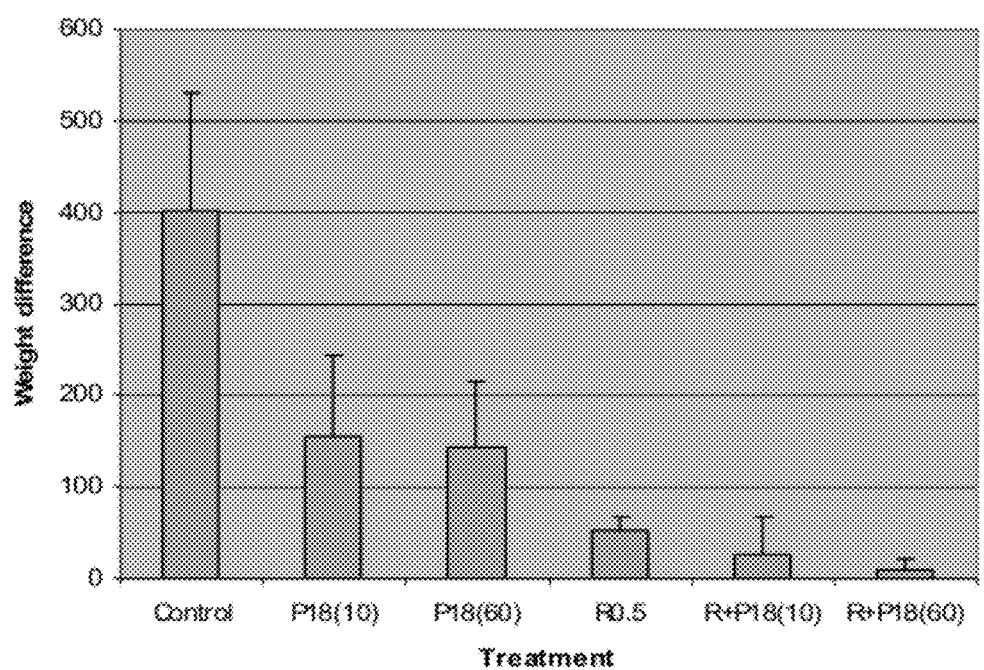
FIG. 8 shows the growth of orthotopic renal cancer xenografts in the present of control peptide (scrambled peptide, SEQ ID NO:51), P18 (18-mer peptide, SEQ ID NO:2), rapamycin (R) and the combination of rapamycin and P18.

P18 Suppresses the Growth of Renal Cell Carcinoma and Metastases in Orthtopic Xenigraft Model and Cooperates with Rapamycin Mouse renal carcinoma cells (Renca, ATCC) were injected under the kidney capsule (0.5×10$^6$/site). Animals were randomly divided into 6 groups (8 per group) and the treatment started 5 days after inoculation (intraperitoneal injections). The following treatment groups were included: P18 (SEQ ID NO:2; 10 mg/kg); P18 (60 mg/kg); Rapamycin (R, 0.5 mg/kg); R+P18 (10 mg/kg) and R+P18 (60 mg/kg). The control group was treated with scrambled peptide, YFNGRSSPSNTNTYYVDRL (SEQ ID NO:51). After 17 days of treatment both kidneys were removed. To assess tumor growth, the weight of healthy kidney was subtracted from the weight of tumor-inoculated kidney, for each animal. The difference represents the weight of the tumor. Average difference with SD meanings per group is shown in FIG. 8. Note significant (P<0.0003) decrease in tumor weight in P18-treated animals. Also note that the combination of Rapa (0.5 mg/kg) and P18 (60 mg/kg) completely abolished tumor growth (no difference from the basal variations in kidney weight (P=0.12). In the figure, the control peptide is the scrambled peptide, (SEQ ID NO:51), P18 is the 18-mer peptide (SEQ ID NO:2), and R is rapamycin.

Figure 9:
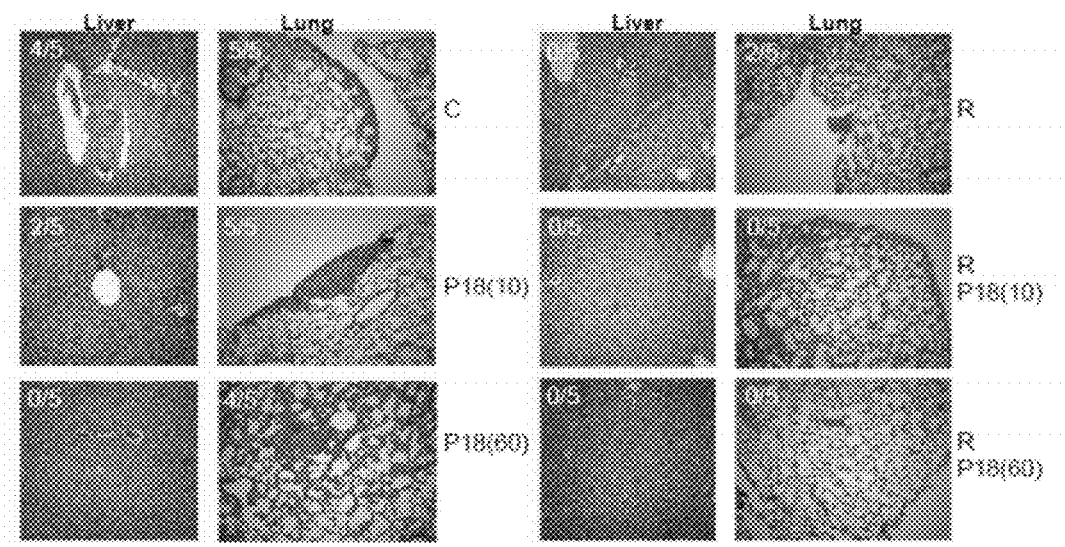
FIG. 9 shows metastases formation by orthotopic renal cancer xenografts as described in Example 1. In this figure: Control=scrambled peptide, P18=18mer (SEQ ID NO:2), R=rapamycin. The incidence (affected organs) is shown in the left upper corner.

Metastases formation was also examined in the liver and lungs of the in the control treated animals and the groups treated with P18 and scrambled peptide (FIG. 9). The % affected organs is indicated under the representative images. Note that P18 treatment eradicated liver metastases, while combination treatment abolished lung metastases.

All publications and patents mentioned in the above specification are herein incorporated by reference as if expressly set forth herein. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the invention.

We claim:

1. A method of inhibiting angiogenesis, comprising: contacting a tissue exhibiting angiogenesis with a composition comprising an isolated peptide under conditions such that angiogenesis is decreased in said tissue, wherein said peptide consists of an amino acid sequence selected from the group consisting of: SEQ ID NOs:2, 12, 13, 22, 23, 33, 34, 41, 42, 52, 53, 62, 63, 73, 74, 84, and 85.

2. The method of claim 1, wherein said peptide consists of the amino acid sequence shown in SEQ ID NO:2 or SEQ ID NO:52.

3. The method of claim 2, wherein said composition further comprises a fluorescent compound.

4. The method of claim 1, wherein said composition further comprises an anti-cancer agent different from said peptide.

5. The method of claim 4, wherein said anti-cancer agent comprises rapamycin.

6. The method of claim 1, wherein said composition further comprises a physiological tolerable buffer.

7. The method of claim 1, wherein said composition further comprises an anti-angiogenic agent different from said peptide.

8. The method of claim 1, further comprising the step of administering a second agent to said tissue.

9. The method of claim 1, wherein said tissue is cancerous tissue.

10. The method of claim 1, wherein said tissue is in a subject.

* * * * *

SEQUENCE LISTING

<160> NUMBER OF SEQ ID NOS: 101

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Asp Leu Tyr Arg Val Arg Ser Ser Thr Ser Pro Thr Thr Asn
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Asn Phe Gly Tyr Asp Leu Tyr Arg Val Arg Ser Ser Thr Ser Pro Thr
1               5                   10                  15

Thr Asn

<210> SEQ ID NO 3
<211> LENGTH: 23
<212> TYPE: PRT
<213> ORGANISM: Artificial Sequence
<220> FEATURE:
<223> OTHER INFORMATION: Synthetic

<400> SEQUENCE: 3

Ala Ala Ala Val Ser Asn Phe Gly Tyr Asp Leu Tyr Arg Val Arg Ser
1               5                   10                  15

Ser Thr Ser Pro Thr Thr Asn
            20

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Phe Gly Tyr Asp Leu Tyr Arg Val Arg Ser Ser Thr Ser Pro Thr Thr
1               5                   10                  15

Asn

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Gly Tyr Asp Leu Tyr Arg Val Arg Ser Ser Thr Ser Pro Thr Thr Asn
1               5                   10                  15

<210> SEQ ID NO 6
<211> LENGTH: 15
<212> TYPE: PRT

```
<213> ORGANISM: Artificial Sequence
<220> FEATURE:
<223> OTHER INFORMATION: Synthetic

<400> SEQUENCE: 6

Tyr Asp Leu Tyr Arg Val Arg Ser Ser Thr Ser Pro Thr Thr Asn
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

Asn Phe Gly Tyr Asp Leu Tyr Arg Val Arg Ser Ser Thr Ser Pro Thr
1               5                   10                  15

Thr

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Asn Phe Gly Tyr Asp Leu Tyr Arg Val Arg Ser Ser Thr Ser Pro Thr
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Asn Phe Gly Tyr Asp Leu Tyr Arg Val Arg Ser Ser Thr Ser Pro
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Asn Phe Gly Tyr Asp Leu Tyr Arg Val Arg Ser Ser Thr Ser
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Asn Phe Gly Tyr Asp Leu Tyr Arg Val Arg Ser Ser Thr
1               5                   10

<210> SEQ ID NO 12
<211> LENGTH: 19
<212> TYPE: PRT
```

```
<213> ORGANISM: Artificial Sequence
<220> FEATURE:
<223> OTHER INFORMATION: Synthetic

<400> SEQUENCE: 12

Ser Asn Phe Gly Tyr Asp Leu Tyr Arg Val Arg Ser Ser Thr Ser Pro
1               5                   10                  15

Thr Thr Asn

<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Val Ser Asn Phe Gly Tyr Asp Leu Tyr Arg Val Arg Ser Ser Thr Ser
1               5                   10                  15

Pro Thr Thr Asn
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic

<400> SEQUENCE: 14

Ala Val Ser Asn Phe Gly Tyr Asp Leu Tyr Arg Val Arg Ser Ser Thr
1               5                   10                  15

Ser Pro Thr Thr Asn
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

Ala Ala Val Ser Asn Phe Gly Tyr Asp Leu Tyr Arg Val Arg Ser Ser
1               5                   10                  15

Thr Ser Pro Thr Thr Asn
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic

<400> SEQUENCE: 16

Leu Ala Ala Ala Val Ser Asn Phe Gly Tyr Asp Leu Tyr Arg Val Arg
1               5                   10                  15

Ser Ser Thr Ser Pro Thr Thr Asn
            20

<210> SEQ ID NO 17
<211> LENGTH: 25
<212> TYPE: PRT
<213> ORGANISM: Artificial Sequence
```

```
<220> FEATURE:
<223> OTHER INFORMATION: Synthetic

<400> SEQUENCE: 17

Lys Leu Ala Ala Ala Val Ser Asn Phe Gly Tyr Asp Leu Tyr Arg Val
1               5                   10                  15

Arg Ser Ser Thr Ser Pro Thr Thr Asn
            20                  25

<210> SEQ ID NO 18
<211> LENGTH: 26
<212> TYPE: PRT
<213> ORGANISM: Artificial Sequence
<220> FEATURE:
<223> OTHER INFORMATION: Synthetic

<400> SEQUENCE: 18

Asn Lys Leu Ala Ala Ala Val Ser Asn Phe Gly Tyr Asp Leu Tyr Arg
1               5                   10                  15

Val Arg Ser Ser Thr Ser Pro Thr Thr Asn
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic

<400> SEQUENCE: 19

Val Asn Lys Leu Ala Ala Ala Val Ser Asn Phe Gly Tyr Asp Leu Tyr
1               5                   10                  15

Arg Val Arg Ser Ser Thr Ser Pro Thr Thr Asn
            20                  25

<210> SEQ ID NO 20
<211> LENGTH: 28
<212> TYPE: PRT
<213> ORGANISM: Artificial Sequence
<220> FEATURE:
<223> OTHER INFORMATION: Synthetic

<400> SEQUENCE: 20

Pro Val Asn Lys Leu Ala Ala Ala Val Ser Asn Phe Gly Tyr Asp Leu
1               5                   10                  15

Tyr Arg Val Arg Ser Ser Thr Ser Pro Thr Thr Asn
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic

<400> SEQUENCE: 21

Val Pro Val Asn Lys Leu Ala Ala Ala Val Ser Asn Phe Gly Tyr Asp
1               5                   10                  15

Leu Tyr Arg Val Arg Ser Ser Thr Ser Pro Thr Thr Asn
            20                  25

<210> SEQ ID NO 22
<211> LENGTH: 19
<212> TYPE: PRT
<213> ORGANISM: Artificial Sequence
```

```
<220> FEATURE:
<223> OTHER INFORMATION: Synthetic

<400> SEQUENCE: 22

Asn Phe Gly Tyr Asp Leu Tyr Arg Val Arg Ser Ser Thr Ser Pro Thr
1               5                   10                  15

Thr Asn Val

<210> SEQ ID NO 23
<211> LENGTH: 20
<212> TYPE: PRT
<213> ORGANISM: Artificial Sequence
<220> FEATURE:
<223> OTHER INFORMATION: Synthetic

<400> SEQUENCE: 23

Asn Phe Gly Tyr Asp Leu Tyr Arg Val Arg Ser Ser Thr Ser Pro Thr
1               5                   10                  15

Thr Asn Val Leu
            20

<210> SEQ ID NO 24
<211> LENGTH: 21
<212> TYPE: PRT
<213> ORGANISM: Artificial Sequence
<220> FEATURE:
<223> OTHER INFORMATION: Synthetic

<400> SEQUENCE: 24

Asn Phe Gly Tyr Asp Leu Tyr Arg Val Arg Ser Ser Thr Ser Pro Thr
1               5                   10                  15

Thr Asn Val Leu Leu
            20

<210> SEQ ID NO 25
<211> LENGTH: 22
<212> TYPE: PRT
<213> ORGANISM: Artificial Sequence
<220> FEATURE:
<223> OTHER INFORMATION: Synthetic

<400> SEQUENCE: 25

Asn Phe Gly Tyr Asp Leu Tyr Arg Val Arg Ser Ser Thr Ser Pro Thr
1               5                   10                  15

Thr Asn Val Leu Leu Ser
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic

<400> SEQUENCE: 26

Asn Phe Gly Tyr Asp Leu Tyr Arg Val Arg Ser Ser Thr Ser Pro Thr
1               5                   10                  15

Thr Asn Val Leu Leu Ser Pro
            20

<210> SEQ ID NO 27
<211> LENGTH: 24
<212> TYPE: PRT
<213> ORGANISM: Artificial Sequence
<220> FEATURE:
```

<223> OTHER INFORMATION: Synthetic

<400> SEQUENCE: 27

Asn Phe Gly Tyr Asp Leu Tyr Arg Val Arg Ser Ser Thr Ser Pro Thr
1               5                   10                  15

Thr Asn Val Leu Leu Ser Pro Leu
            20

<210> SEQ ID NO 28
<211> LENGTH: 25
<212> TYPE: PRT
<213> ORGANISM: Artificial Sequence
<220> FEATURE:
<223> OTHER INFORMATION: Synthetic

<400> SEQUENCE: 28

Asn Phe Gly Tyr Asp Leu Tyr Arg Val Arg Ser Ser Thr Ser Pro Thr
1               5                   10                  15

Thr Asn Val Leu Leu Ser Pro Leu Ser
            20                  25

<210> SEQ ID NO 29
<211> LENGTH: 26
<212> TYPE: PRT
<213> ORGANISM: Artificial Sequence
<220> FEATURE:
<223> OTHER INFORMATION: Synthetic

<400> SEQUENCE: 29

Asn Phe Gly Tyr Asp Leu Tyr Arg Val Arg Ser Ser Thr Ser Pro Thr
1               5                   10                  15

Thr Asn Val Leu Leu Ser Pro Leu Ser Val
            20                  25

<210> SEQ ID NO 30
<211> LENGTH: 27
<212> TYPE: PRT
<213> ORGANISM: Artificial Sequence
<220> FEATURE:
<223> OTHER INFORMATION: Synthetic

<400> SEQUENCE: 30

Asn Phe Gly Tyr Asp Leu Tyr Arg Val Arg Ser Ser Thr Ser Pro Thr
1               5                   10                  15

Thr Asn Val Leu Leu Ser Pro Leu Ser Val Ala
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthetic

<400> SEQUENCE: 31

Asn Phe Gly Tyr Asp Leu Tyr Arg Val Arg Ser Ser Thr Ser Pro Thr
1               5                   10                  15

Thr Asn Val Leu Leu Ser Pro Leu Ser Val Ala Thr
            20                  25

<210> SEQ ID NO 32
<211> LENGTH: 29
<212> TYPE: PRT
<213> ORGANISM: Artificial Sequence
<220> FEATURE:

<223> OTHER INFORMATION: Synthetic

<400> SEQUENCE: 32

Asn Phe Gly Tyr Asp Leu Tyr Arg Val Arg Ser Ser Thr Ser Pro Thr
1               5                   10                  15
Thr Asn Val Leu Leu Ser Pro Leu Ser Val Ala Thr Ala
            20                  25

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

Ser Asn Phe Gly Tyr Asp Leu Tyr Arg Val Arg Ser Ser Thr Ser Pro
1               5                   10                  15
Thr Thr Asn Val
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic

<400> SEQUENCE: 34

Val Ser Asn Phe Gly Tyr Asp Leu Tyr Arg Val Arg Ser Ser Thr Ser
1               5                   10                  15
Pro Thr Thr Asn Val Leu
            20

<210> SEQ ID NO 35
<211> LENGTH: 24
<212> TYPE: PRT
<213> ORGANISM: Artificial Sequence
<220> FEATURE:
<223> OTHER INFORMATION: Synthetic

<400> SEQUENCE: 35

Ala Val Ser Asn Phe Gly Tyr Asp Leu Tyr Arg Val Arg Ser Ser Thr
1               5                   10                  15
Ser Pro Thr Thr Asn Val Leu Leu
            20

<210> SEQ ID NO 36
<211> LENGTH: 26
<212> TYPE: PRT
<213> ORGANISM: Artificial Sequence
<220> FEATURE:
<223> OTHER INFORMATION: Synthetic

<400> SEQUENCE: 36

Ala Ala Val Ser Asn Phe Gly Tyr Asp Leu Tyr Arg Val Arg Ser Ser
1               5                   10                  15
Thr Ser Pro Thr Thr Asn Val Leu Leu Ser
            20                  25

<210> SEQ ID NO 37
<211> LENGTH: 28
<212> TYPE: PRT
<213> ORGANISM: Artificial Sequence
<220> FEATURE:

-continued

<223> OTHER INFORMATION: Synthetic

<400> SEQUENCE: 37

Ala Ala Ala Val Ser Asn Phe Gly Tyr Asp Leu Tyr Arg Val Arg Ser
1               5                   10                  15
Ser Thr Ser Pro Thr Thr Asn Val Leu Leu Ser Pro
            20                  25

<210> SEQ ID NO 38
<211> LENGTH: 30
<212> TYPE: PRT
<213> ORGANISM: Artificial Sequence
<220> FEATURE:
<223> OTHER INFORMATION: Synthetic

<400> SEQUENCE: 38

Leu Ala Ala Ala Val Ser Asn Phe Gly Tyr Asp Leu Tyr Arg Val Arg
1               5                   10                  15
Ser Ser Thr Ser Pro Thr Thr Asn Val Leu Leu Ser Pro Leu
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Synthetic

<400> SEQUENCE: 39

Lys Leu Ala Ala Ala Val Ser Asn Phe Gly Tyr Asp Leu Tyr Arg Val
1               5                   10                  15
Arg Ser Ser Thr Ser Pro Thr Thr Asn Val Leu Leu Ser Pro Leu Ser
            20                  25                  30

<210> SEQ ID NO 40
<211> LENGTH: 34
<212> TYPE: PRT
<213> ORGANISM: Artificial Sequence
<220> FEATURE:
<223> OTHER INFORMATION: Synthetic

<400> SEQUENCE: 40

Asn Lys Leu Ala Ala Ala Val Ser Asn Phe Gly Tyr Asp Leu Tyr Arg
1               5                   10                  15
Val Arg Ser Ser Thr Ser Pro Thr Thr Asn Val Leu Leu Ser Pro Leu
            20                  25                  30
Ser Val

<210> SEQ ID NO 41
<211> LENGTH: 21
<212> TYPE: PRT
<213> ORGANISM: Artificial Sequence
<220> FEATURE:
<223> OTHER INFORMATION: Synthetic

<400> SEQUENCE: 41

Ser Asn Phe Gly Tyr Asp Leu Tyr Arg Val Arg Ser Ser Thr Ser Pro
1               5                   10                  15
Thr Thr Asn Val Leu
            20

<210> SEQ ID NO 42
<211> LENGTH: 21
<212> TYPE: PRT

```
<213> ORGANISM: Artificial Sequence
<220> FEATURE:
<223> OTHER INFORMATION: Synthetic

<400> SEQUENCE: 42

Val Ser Asn Phe Gly Tyr Asp Leu Tyr Arg Val Arg Ser Ser Thr Ser
1               5                   10                  15

Pro Thr Thr Asn Val
            20

<210> SEQ ID NO 43
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 43

Xaa Asn Phe Gly Tyr Asp Leu Tyr Arg Val Arg Ser Ser Thr Ser Pro
1               5                   10                  15

Thr Thr Asn

<210> SEQ ID NO 44
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 44

Xaa Xaa Asn Phe Gly Tyr Asp Leu Tyr Arg Val Arg Ser Ser Thr Ser
1               5                   10                  15

Pro Thr Thr Asn
            20

<210> SEQ ID NO 45
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: Xaa can be any naturally occurring amino acid

<400> SEQUENCE: 45

Asn Phe Gly Tyr Asp Leu Tyr Arg Val Arg Ser Ser Thr Ser Pro Thr
1               5                   10                  15

Thr Asn Xaa

<210> SEQ ID NO 46
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
```

<223> OTHER INFORMATION: Xaa can be any naturally occurring amino acid

<400> SEQUENCE: 46

```
Asn Phe Gly Tyr Asp Leu Tyr Arg Val Arg Ser Ser Thr Ser Pro Thr
1               5                   10                  15

Thr Asn Xaa Xaa
            20
```

<210> SEQ ID NO 47
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 47

```
Xaa Asn Phe Gly Tyr Asp Leu Tyr Arg Val Arg Ser Ser Thr Ser Pro
1               5                   10                  15

Thr Thr Asn Xaa
            20
```

<210> SEQ ID NO 48
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 48

```
Xaa Asn Phe Gly Tyr Asp Leu Tyr Arg Val Arg Ser Ser Thr Ser Pro
1               5                   10                  15

Thr Thr Asn Xaa Xaa
            20
```

<210> SEQ ID NO 49
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 49

```
Xaa Xaa Asn Phe Gly Tyr Asp Leu Tyr Arg Val Arg Ser Ser Thr Ser
1               5                   10                  15

Pro Thr Thr Asn Xaa Xaa
```

<210> SEQ ID NO 50
<211> LENGTH: 419
<212> TYPE: PRT
<213> ORGANISM: Artificial Sequence
<220> FEATURE:
<223> OTHER INFORMATION: Synthetic

<400> SEQUENCE: 50

```
Met Gln Ala Leu Val Leu Leu Leu Cys Ile Gly Ala Leu Leu Gly His
 1               5                  10                  15
Ser Ser Cys Gln Asn Pro Ala Ser Pro Pro Glu Glu Gly Ser Pro Asp
                20                  25                  30
Pro Asp Ser Thr Gly Ala Leu Val Glu Glu Glu Asp Pro Phe Phe Lys
            35                  40                  45
Val Pro Val Asn Lys Leu Ala Ala Ala Val Ser Asn Phe Gly Tyr Asp
        50                  55                  60
Leu Tyr Arg Val Arg Ser Ser Thr Ser Pro Thr Thr Asn Val Leu Leu
 65                 70                  75                  80
Ser Pro Leu Ser Val Ala Thr Ala Leu Ser Ala Leu Ser Leu Gly Ala
                85                  90                  95
Glu Gln Arg Thr Glu Ser Ile Ile His Arg Ala Leu Tyr Tyr Asp Leu
            100                 105                 110
Ile Ser Ser Pro Asp Ile His Gly Thr Tyr Lys Glu Leu Leu Asp Thr
        115                 120                 125
Val Thr Ala Pro Gln Lys Asn Leu Lys Ser Ala Ser Arg Ile Val Phe
130                 135                 140
Glu Lys Lys Leu Arg Ile Lys Ser Ser Phe Val Ala Pro Leu Glu Lys
145                 150                 155                 160
Ser Tyr Gly Thr Arg Pro Arg Val Leu Thr Gly Asn Pro Arg Leu Asp
                165                 170                 175
Leu Gln Glu Ile Asn Asn Trp Val Gln Ala Gln Met Lys Gly Lys Leu
            180                 185                 190
Ala Arg Ser Thr Lys Glu Ile Pro Asp Glu Ile Ser Ile Leu Leu Leu
        195                 200                 205
Gly Val Ala His Phe Lys Gly Gln Trp Val Thr Lys Phe Asp Ser Arg
    210                 215                 220
Lys Thr Ser Leu Glu Asp Phe Tyr Leu Asp Glu Glu Arg Thr Val Arg
225                 230                 235                 240
Val Pro Met Met Ser Asp Pro Lys Ala Val Leu Arg Tyr Gly Leu Asp
                245                 250                 255
Ser Asp Leu Ser Cys Lys Ile Ala Gln Leu Pro Leu Thr Gly Ser Met
            260                 265                 270
Ser Ile Ile Phe Phe Leu Pro Leu Lys Val Thr Gln Asn Leu Thr Leu
        275                 280                 285
Ile Glu Glu Ser Leu Thr Ser Glu Phe Ile His Asp Ile Asp Arg Glu
    290                 295                 300
Leu Lys Thr Val Gln Ala Val Leu Thr Val Pro Lys Leu Lys Leu Ser
305                 310                 315                 320
Tyr Glu Gly Glu Val Thr Lys Ser Leu Gln Glu Met Lys Leu Gln Ser
                325                 330                 335
Leu Phe Asp Ser Pro Asp Phe Ser Lys Ile Thr Gly Lys Pro Ile Lys
            340                 345                 350
Leu Thr Gln Val Glu His Arg Ala Gly Phe Glu Trp Asn Glu Asp Gly
        355                 360                 365
```

-continued

```
Ala Gly Thr Thr Pro Ser Pro Gly Leu Gln Pro Ala His Leu Thr Phe
        370                 375                 380
Pro Leu Asp Tyr His Leu Asn Gln Pro Phe Ile Phe Val Leu Arg Asp
385                 390                 395                 400
Thr Asp Thr Gly Ala Leu Leu Phe Ile Gly Lys Ile Leu Asp Pro Arg
                405                 410                 415
Gly Pro Leu

<210> SEQ ID NO 51
<211> LENGTH: 19
<212> TYPE: PRT
<213> ORGANISM: Artificial Sequence
<220> FEATURE:
<223> OTHER INFORMATION: Synthetic

<400> SEQUENCE: 51

Tyr Phe Asn Gly Arg Ser Ser Pro Ser Asn Thr Asn Thr Tyr Tyr Val
1               5                   10                  15
Asp Arg Leu

<210> SEQ ID NO 52
<211> LENGTH: 14
<212> TYPE: PRT
<213> ORGANISM: Artificial Sequence
<220> FEATURE:
<223> OTHER INFORMATION: Synthetic

<400> SEQUENCE: 52

Asp Leu Tyr Arg Val Arg Ser Ser Met Ser Pro Thr Thr Asn
1               5                   10

<210> SEQ ID NO 53
<211> LENGTH: 18
<212> TYPE: PRT
<213> ORGANISM: Artificial Sequence
<220> FEATURE:
<223> OTHER INFORMATION: Synthetic

<400> SEQUENCE: 53

Asn Phe Gly Tyr Asp Leu Tyr Arg Val Arg Ser Ser Met Ser Pro Thr
1               5                   10                  15
Thr Asn

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Phe Gly Tyr Asp Leu Tyr Arg Val Arg Ser Ser Met Ser Pro Thr Thr
1               5                   10                  15
Asn

<210> SEQ ID NO 55
<211> LENGTH: 16
<212> TYPE: PRT
<213> ORGANISM: Artificial Sequence
<220> FEATURE:
<223> OTHER INFORMATION: Synthetic

<400> SEQUENCE: 55
```

```
Gly Tyr Asp Leu Tyr Arg Val Arg Ser Ser Met Ser Pro Thr Thr Asn
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

```
Tyr Asp Leu Tyr Arg Val Arg Ser Ser Met Ser Pro Thr Thr Asn
1               5                   10                  15
```

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

```
Asn Phe Gly Tyr Asp Leu Tyr Arg Val Arg Ser Ser Met Ser Pro Thr
1               5                   10                  15

Thr
```

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

```
Asn Phe Gly Tyr Asp Leu Tyr Arg Val Arg Ser Ser Met Ser Pro Thr
1               5                   10                  15
```

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

```
Asn Phe Gly Tyr Asp Leu Tyr Arg Val Arg Ser Ser Met Ser Pro
1               5                   10                  15
```

<210> SEQ ID NO 60
<211> LENGTH: 14
<212> TYPE: PRT
<213> ORGANISM: Artificial Sequence
<220> FEATURE:
<223> OTHER INFORMATION: Synthetic

<400> SEQUENCE: 60

```
Asn Phe Gly Tyr Asp Leu Tyr Arg Val Arg Ser Ser Met Ser
1               5                   10
```

<210> SEQ ID NO 61
<211> LENGTH: 13
<212> TYPE: PRT
<213> ORGANISM: Artificial Sequence
<220> FEATURE:
<223> OTHER INFORMATION: Synthetic

<400> SEQUENCE: 61

```
Asn Phe Gly Tyr Asp Leu Tyr Arg Val Arg Ser Ser Met
1               5                   10
```

<210> SEQ ID NO 62
<211> LENGTH: 19
<212> TYPE: PRT
<213> ORGANISM: Artificial Sequence
<220> FEATURE:
<223> OTHER INFORMATION: Synthetic

<400> SEQUENCE: 62

```
Ser Asn Phe Gly Tyr Asp Leu Tyr Arg Val Arg Ser Ser Met Ser Pro
1               5                   10                  15

Thr Thr Asn
```

<210> SEQ ID NO 63
<211> LENGTH: 20
<212> TYPE: PRT
<213> ORGANISM: Artificial Sequence
<220> FEATURE:
<223> OTHER INFORMATION: Synthetic

<400> SEQUENCE: 63

```
Val Ser Asn Phe Gly Tyr Asp Leu Tyr Arg Val Arg Ser Ser Met Ser
1               5                   10                  15

Pro Thr Thr Asn
            20
```

<210> SEQ ID NO 64
<211> LENGTH: 21
<212> TYPE: PRT
<213> ORGANISM: Artificial Sequence
<220> FEATURE:
<223> OTHER INFORMATION: Synthetic

<400> SEQUENCE: 64

```
Ala Val Ser Asn Phe Gly Tyr Asp Leu Tyr Arg Val Arg Ser Ser Met
1               5                   10                  15

Ser Pro Thr Thr Asn
            20
```

<210> SEQ ID NO 65
<211> LENGTH: 22
<212> TYPE: PRT
<213> ORGANISM: Artificial Sequence
<220> FEATURE:
<223> OTHER INFORMATION: Synthetic

<400> SEQUENCE: 65

```
Ala Ala Val Ser Asn Phe Gly Tyr Asp Leu Tyr Arg Val Arg Ser Ser
1               5                   10                  15

Met Ser Pro Thr Thr Asn
            20
```

<210> SEQ ID NO 66
<211> LENGTH: 23
<212> TYPE: PRT
<213> ORGANISM: Artificial Sequence
<220> FEATURE:
<223> OTHER INFORMATION: Synthetic

<400> SEQUENCE: 66

```
Ala Ala Ala Val Ser Asn Phe Gly Tyr Asp Leu Tyr Arg Val Arg Ser
1               5                   10                  15

Ser Met Ser Pro Thr Thr Asn
```

```
<210> SEQ ID NO 67
<211> LENGTH: 24
<212> TYPE: PRT
<213> ORGANISM: Artificial Sequence
<220> FEATURE:
<223> OTHER INFORMATION: Synthetic

<400> SEQUENCE: 67

Leu Ala Ala Ala Val Ser Asn Phe Gly Tyr Asp Leu Tyr Arg Val Arg
1               5                   10                  15

Ser Ser Met Ser Pro Thr Thr Asn
            20

<210> SEQ ID NO 68
<211> LENGTH: 25
<212> TYPE: PRT
<213> ORGANISM: Artificial Sequence
<220> FEATURE:
<223> OTHER INFORMATION: Synthetic

<400> SEQUENCE: 68

Lys Leu Ala Ala Ala Val Ser Asn Phe Gly Tyr Asp Leu Tyr Arg Val
1               5                   10                  15

Arg Ser Ser Met Ser Pro Thr Thr Asn
            20                  25

<210> SEQ ID NO 69
<211> LENGTH: 26
<212> TYPE: PRT
<213> ORGANISM: Artificial Sequence
<220> FEATURE:
<223> OTHER INFORMATION: Synthetic

<400> SEQUENCE: 69

Asn Lys Leu Ala Ala Ala Val Ser Asn Phe Gly Tyr Asp Leu Tyr Arg
1               5                   10                  15

Val Arg Ser Ser Met Ser Pro Thr Thr Asn
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic

<400> SEQUENCE: 70

Val Asn Lys Leu Ala Ala Ala Val Ser Asn Phe Gly Tyr Asp Leu Tyr
1               5                   10                  15

Arg Val Arg Ser Ser Met Ser Pro Thr Thr Asn
            20                  25

<210> SEQ ID NO 71
<211> LENGTH: 28
<212> TYPE: PRT
<213> ORGANISM: Artificial Sequence
<220> FEATURE:
<223> OTHER INFORMATION: Synthetic

<400> SEQUENCE: 71

Pro Val Asn Lys Leu Ala Ala Ala Val Ser Asn Phe Gly Tyr Asp Leu
1               5                   10                  15

Tyr Arg Val Arg Ser Ser Met Ser Pro Thr Thr Asn
```

```
<210> SEQ ID NO 72
<211> LENGTH: 29
<212> TYPE: PRT
<213> ORGANISM: Artificial Sequence
<220> FEATURE:
<223> OTHER INFORMATION: Synthetic

<400> SEQUENCE: 72
```

Val Pro Val Asn Lys Leu Ala Ala Ala Val Ser Asn Phe Gly Tyr Asp
1               5                   10                  15

Leu Tyr Arg Val Arg Ser Ser Met Ser Pro Thr Thr Asn
            20                  25

```
<210> SEQ ID NO 73
<211> LENGTH: 19
<212> TYPE: PRT
<213> ORGANISM: Artificial Sequence
<220> FEATURE:
<223> OTHER INFORMATION: Synthetic

<400> SEQUENCE: 73
```

Asn Phe Gly Tyr Asp Leu Tyr Arg Val Arg Ser Ser Met Ser Pro Thr
1               5                   10                  15

Thr Asn Val

```
<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74
```

Asn Phe Gly Tyr Asp Leu Tyr Arg Val Arg Ser Ser Met Ser Pro Thr
1               5                   10                  15

Thr Asn Val Leu
            20

```
<210> SEQ ID NO 75
<211> LENGTH: 21
<212> TYPE: PRT
<213> ORGANISM: Artificial Sequence
<220> FEATURE:
<223> OTHER INFORMATION: Synthetic

<400> SEQUENCE: 75
```

Asn Phe Gly Tyr Asp Leu Tyr Arg Val Arg Ser Ser Met Ser Pro Thr
1               5                   10                  15

Thr Asn Val Leu Leu
            20

```
<210> SEQ ID NO 76
<211> LENGTH: 22
<212> TYPE: PRT
<213> ORGANISM: Artificial Sequence
<220> FEATURE:
<223> OTHER INFORMATION: Synthetic

<400> SEQUENCE: 76
```

Asn Phe Gly Tyr Asp Leu Tyr Arg Val Arg Ser Ser Met Ser Pro Thr
1               5                   10                  15

Thr Asn Val Leu Leu Ser
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic

<400> SEQUENCE: 77

Asn Phe Gly Tyr Asp Leu Tyr Arg Val Arg Ser Ser Met Ser Pro Thr
1               5                   10                  15

Thr Asn Val Leu Leu Ser Pro
            20

<210> SEQ ID NO 78
<211> LENGTH: 24
<212> TYPE: PRT
<213> ORGANISM: Artificial Sequence
<220> FEATURE:
<223> OTHER INFORMATION: Synthetic

<400> SEQUENCE: 78

Asn Phe Gly Tyr Asp Leu Tyr Arg Val Arg Ser Ser Met Ser Pro Thr
1               5                   10                  15

Thr Asn Val Leu Leu Ser Pro Leu
            20

<210> SEQ ID NO 79
<211> LENGTH: 25
<212> TYPE: PRT
<213> ORGANISM: Artificial Sequence
<220> FEATURE:
<223> OTHER INFORMATION: Synthetic

<400> SEQUENCE: 79

Asn Phe Gly Tyr Asp Leu Tyr Arg Val Arg Ser Ser Met Ser Pro Thr
1               5                   10                  15

Thr Asn Val Leu Leu Ser Pro Leu Ser
            20                  25

<210> SEQ ID NO 80
<211> LENGTH: 26
<212> TYPE: PRT
<213> ORGANISM: Artificial Sequence
<220> FEATURE:
<223> OTHER INFORMATION: Synthetic

<400> SEQUENCE: 80

Asn Phe Gly Tyr Asp Leu Tyr Arg Val Arg Ser Ser Met Ser Pro Thr
1               5                   10                  15

Thr Asn Val Leu Leu Ser Pro Leu Ser Val
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic

<400> SEQUENCE: 81

Asn Phe Gly Tyr Asp Leu Tyr Arg Val Arg Ser Ser Met Ser Pro Thr
1               5                   10                  15

Thr Asn Val Leu Leu Ser Pro Leu Ser Val Ala
            20                  25

-continued

<210> SEQ ID NO 82
<211> LENGTH: 28
<212> TYPE: PRT
<213> ORGANISM: Artificial Sequence
<220> FEATURE:
<223> OTHER INFORMATION: Synthetic

<400> SEQUENCE: 82

Asn Phe Gly Tyr Asp Leu Tyr Arg Val Arg Ser Ser Met Ser Pro Thr
1               5                   10                  15
Thr Asn Val Leu Leu Ser Pro Leu Ser Val Ala Thr
            20                  25

<210> SEQ ID NO 83
<211> LENGTH: 29
<212> TYPE: PRT
<213> ORGANISM: Artificial Sequence
<220> FEATURE:
<223> OTHER INFORMATION: Synthetic

<400> SEQUENCE: 83

Asn Phe Gly Tyr Asp Leu Tyr Arg Val Arg Ser Ser Met Ser Pro Thr
1               5                   10                  15
Thr Asn Val Leu Leu Ser Pro Leu Ser Val Ala Thr Ala
            20                  25

<210> SEQ ID NO 84
<211> LENGTH: 20
<212> TYPE: PRT
<213> ORGANISM: Artificial Sequence
<220> FEATURE:
<223> OTHER INFORMATION: Synthetic

<400> SEQUENCE: 84

Ser Asn Phe Gly Tyr Asp Leu Tyr Arg Val Arg Ser Ser Met Ser Pro
1               5                   10                  15
Thr Thr Asn Val
            20

<210> SEQ ID NO 85
<211> LENGTH: 22
<212> TYPE: PRT
<213> ORGANISM: Artificial Sequence
<220> FEATURE:
<223> OTHER INFORMATION: Synthetic

<400> SEQUENCE: 85

Val Ser Asn Phe Gly Tyr Asp Leu Tyr Arg Val Arg Ser Ser Met Ser
1               5                   10                  15
Pro Thr Thr Asn Val Leu
            20

<210> SEQ ID NO 86
<211> LENGTH: 24
<212> TYPE: PRT
<213> ORGANISM: Artificial Sequence
<220> FEATURE:
<223> OTHER INFORMATION: Synthetic

<400> SEQUENCE: 86

Ala Val Ser Asn Phe Gly Tyr Asp Leu Tyr Arg Val Arg Ser Ser Met
1               5                   10                  15
Ser Pro Thr Thr Asn Val Leu Leu
            20

<210> SEQ ID NO 87
<211> LENGTH: 26
<212> TYPE: PRT
<213> ORGANISM: Artificial Sequence
<220> FEATURE:
<223> OTHER INFORMATION: Synthetic

<400> SEQUENCE: 87

Ala Ala Val Ser Asn Phe Gly Tyr Asp Leu Tyr Arg Val Arg Ser Ser
1               5                   10                  15

Met Ser Pro Thr Thr Asn Val Leu Leu Ser
            20                  25

<210> SEQ ID NO 88
<211> LENGTH: 28
<212> TYPE: PRT
<213> ORGANISM: Artificial Sequence
<220> FEATURE:
<223> OTHER INFORMATION: Synthetic

<400> SEQUENCE: 88

Ala Ala Ala Val Ser Asn Phe Gly Tyr Asp Leu Tyr Arg Val Arg Ser
1               5                   10                  15

Ser Met Ser Pro Thr Thr Asn Val Leu Leu Ser Pro
            20                  25

<210> SEQ ID NO 89
<211> LENGTH: 30
<212> TYPE: PRT
<213> ORGANISM: Artificial Sequence
<220> FEATURE:
<223> OTHER INFORMATION: Synthetic

<400> SEQUENCE: 89

Leu Ala Ala Ala Val Ser Asn Phe Gly Tyr Asp Leu Tyr Arg Val Arg
1               5                   10                  15

Ser Ser Met Ser Pro Thr Thr Asn Val Leu Leu Ser Pro Leu
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic

<400> SEQUENCE: 90

Lys Leu Ala Ala Ala Val Ser Asn Phe Gly Tyr Asp Leu Tyr Arg Val
1               5                   10                  15

Arg Ser Ser Met Ser Pro Thr Thr Asn Val Leu Leu Ser Pro Leu Ser
            20                  25                  30

<210> SEQ ID NO 91
<211> LENGTH: 34
<212> TYPE: PRT
<213> ORGANISM: Artificial Sequence
<220> FEATURE:
<223> OTHER INFORMATION: Synthetic

<400> SEQUENCE: 91

Asn Lys Leu Ala Ala Ala Val Ser Asn Phe Gly Tyr Asp Leu Tyr Arg
1               5                   10                  15

Val Arg Ser Ser Met Ser Pro Thr Thr Asn Val Leu Leu Ser Pro Leu
            20                  25                  30

Ser Val

<210> SEQ ID NO 92
<211> LENGTH: 21
<212> TYPE: PRT
<213> ORGANISM: Artificial Sequence
<220> FEATURE:
<223> OTHER INFORMATION: Synthetic

<400> SEQUENCE: 92

Ser Asn Phe Gly Tyr Asp Leu Tyr Arg Val Arg Ser Ser Met Ser Pro
1               5                   10                  15

Thr Thr Asn Val Leu
            20

<210> SEQ ID NO 93
<211> LENGTH: 21
<212> TYPE: PRT
<213> ORGANISM: Artificial Sequence
<220> FEATURE:
<223> OTHER INFORMATION: Synthetic

<400> SEQUENCE: 93

Val Ser Asn Phe Gly Tyr Asp Leu Tyr Arg Val Arg Ser Ser Met Ser
1               5                   10                  15

Pro Thr Thr Asn Val
            20

<210> SEQ ID NO 94
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 94

Xaa Asn Phe Gly Tyr Asp Leu Tyr Arg Val Arg Ser Ser Met Ser Pro
1               5                   10                  15

Thr Thr Asn

<210> SEQ ID NO 95
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 95

Xaa Xaa Asn Phe Gly Tyr Asp Leu Tyr Arg Val Arg Ser Ser Met Ser
1               5                   10                  15

Pro Thr Thr Asn
            20

<210> SEQ ID NO 96
<211> LENGTH: 19
<212> TYPE: PRT
<213> ORGANISM: Artificial Sequence
<220> FEATURE:

<223> OTHER INFORMATION: Synthetic
<220> FEATURE:
<221> NAME/KEY: misc_feature
<222> LOCATION: (19)..(19)
<223> OTHER INFORMATION: Xaa can be any naturally occurring amino acid

<400> SEQUENCE: 96

Asn Phe Gly Tyr Asp Leu Tyr Arg Val Arg Ser Ser Met Ser Pro Thr
1               5                   10                  15

Thr Asn Xaa

<210> SEQ ID NO 97
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: Xaa can be any naturally occurring amino acid

<400> SEQUENCE: 97

Asn Phe Gly Tyr Asp Leu Tyr Arg Val Arg Ser Ser Met Ser Pro Thr
1               5                   10                  15

Thr Asn Xaa Xaa
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 98

Xaa Asn Phe Gly Tyr Asp Leu Tyr Arg Val Arg Ser Ser Met Ser Pro
1               5                   10                  15

Thr Thr Asn Xaa
            20

<210> SEQ ID NO 99
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 99

Xaa Asn Phe Gly Tyr Asp Leu Tyr Arg Val Arg Ser Ser Met Ser Pro
1               5                   10                  15

Thr Thr Asn Xaa Xaa
            20

```
<210> SEQ ID NO 100
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 100

Xaa Xaa Asn Phe Gly Tyr Asp Leu Tyr Arg Val Arg Ser Ser Met Ser
1               5                   10                  15

Pro Thr Thr Asn Xaa Xaa
            20

<210> SEQ ID NO 101
<211> LENGTH: 418
<212> TYPE: PRT
<213> ORGANISM: Artificial Sequence
<220> FEATURE:
<223> OTHER INFORMATION: Synthetic

<400> SEQUENCE: 101

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
            115                 120                 125

Val Thr Ala Arg Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
    195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240
```

-continued

```
Val Pro Met Met Ser Asp Pro Lys Ala Val Leu Arg Tyr Gly Leu Asp
            245             250             255
Ser Asp Leu Ser Cys Lys Ile Ala Gln Leu Pro Leu Thr Gly Ser Met
            260             265             270
Ser Ile Ile Phe Phe Leu Pro Leu Lys Val Thr Gln Asn Leu Thr Leu
            275             280             285
Ile Glu Glu Ser Leu Thr Ser Glu Phe Ile His Asp Ile Asp Arg Glu
        290             295             300
Leu Lys Thr Val Gln Ala Val Leu Thr Val Pro Lys Leu Lys Leu Ser
305             310             315             320
Tyr Glu Gly Glu Val Thr Lys Ser Leu Gln Glu Met Lys Leu Gln Ser
                325             330             335
Leu Phe Asp Ser Pro Asp Phe Ser Lys Ile Thr Gly Lys Pro Ile Lys
            340             345             350
Leu Thr Gln Val Glu His Arg Ala Gly Phe Glu Trp Asn Glu Asp Gly
            355             360             365
Ala Gly Thr Thr Pro Ser Pro Gly Leu Gln Pro Ala His Leu Thr Phe
        370             375             380
Pro Leu Asp Tyr His Leu Asn Gln Pro Phe Ile Phe Val Leu Arg Asp
385             390             395             400
Thr Asp Thr Gly Ala Leu Leu Phe Ile Gly Lys Ile Leu Asp Pro Arg
            405             410             415
Gly Pro
```